(12) United States Patent
Kajihara et al.

(10) Patent No.: US 8,058,394 B2
(45) Date of Patent: Nov. 15, 2011

(54) METHOD FOR PRODUCTION OF PEPTIDE THIOESTER COMPOUND

(75) Inventors: Yasuhiro Kajihara, Yokohama (JP); Naoki Yamamoto, Tokushima (JP); Yuri Nambu, Tokushima (JP); Kazuhiro Fukae, Tokushima (JP); Hiroaki Asai, Tokushima (JP)

(73) Assignee: Otsuka Chemical Co., Ltd., Osaka-shi (JP)

( * ) Notice: Subject to any disclaimer, the term of this patent is extended or adjusted under 35 U.S.C. 154(b) by 499 days.

(21) Appl. No.: 12/295,113

(22) PCT Filed: Mar. 28, 2007

(86) PCT No.: PCT/JP2007/057508
§ 371 (c)(1),
(2), (4) Date: Nov. 25, 2008

(87) PCT Pub. No.: WO2007/114454
PCT Pub. Date: Oct. 11, 2007

(65) Prior Publication Data
US 2009/0137780 A1    May 28, 2009

(30) Foreign Application Priority Data
Mar. 29, 2006  (JP) .................. 2006-092569

(51) Int. Cl.
C07K 1/04  (2006.01)
C07K 1/113  (2006.01)
(52) U.S. Cl. ........................ 530/334; 530/345
(58) Field of Classification Search .......... None
See application file for complete search history.

(56) References Cited

U.S. PATENT DOCUMENTS
7,135,566 B2  11/2006  Kajihara et al.
2004/0181054 A1  9/2004  Kajihara et al.
2005/0222382 A1  10/2005  Kajihara FOREIGN PATENT DOCUMENTS
EP    1 961 764 A1    8/2008
WO   WO 03/008431 A1  1/2003
WO   WO 2004/005330 A1  1/2004
WO   WO 2005/095331 A1  10/2005
WO   WO 2007/063907 A1  6/2007

OTHER PUBLICATIONS

Clippingdale, Andrew B., et al.—"Peptide Thioester Preparation by Fmoc Solid Phase Peptide Synthesis for Use in Native Chemical Ligation", *Journal of Peptide Science*, 6: pp. 225-234; (2000).*
Ingenito, Raffaele, et al.—"Solid Phase Synthesis of Peptide C-Terminal Thioesters by Fmoc/t-Bu Chemistry"—Journal American Chemical Society—pp. 11369-11374.—Nov. 25, 1999.
Mezzato, Stefano, et al.—"An Orthogonal Double-Linker Resin Facilitates the Efficient Solid-Phase Synthesis of Complex-Type N-Glycopeptide Thioesters Suitable for Native Chemical Ligation"—Angew. Chem. Int. Ed.—vol. 44, pp. 1650-1654.—2005.
Futaki, Shiroh, et al.—"Preparation of Peptide Thioesters using Fmoc-Solid-Phase Peptide Synthesis and its Application to the Construction of a Template-Assembled Synthetic Protein (TASP)"—Tetrahedron Letters., vol. 44, pp. 6237-6240.—1997.
Von Eggelkraut-Gottanka, Regula, et al.—"Peptide Thioester Formation Using Standard Fmoc-chemistry"—Tetrahedron Letters 44 (Feb. 28, 2003), pp. 3551-3554.
Mezo, Adam R., et al.—"Oligomerization of Uniquely Folded Mini-Protein Motifs: Development of a Homotrimeric ββα Peptide"—Journal American Chemical Society—(Apr. 6, 2001), pp. 3885-3891.
Riniker, Bernhard, et al.—"A General Strategy for the Synthesis of Large Peptides: The Combined Solid-Phase and Solution Approach."—Tetrahedron Letters vol. 49, No. 41, (Apr. 22, 1993), pp. 9307-9320.
Nakahara, Yoshiaki,—"Problems and Progress in Glycopeptide Synthesis"—Trends in Glycoscience and Glycotechnology, vol. 15, No. 85, (Sep. 2003), pp. 257-273.
Kajihara, Yasuhiro, et al.—"Prompt Chemoenzymatic Synthesis of Diverse Complex-Type Oligosaccharides and Its Application to the Solid-Phase Synthesis of a Glycopeptide with Asn- Linked Sialyl-undeca- and Asialo-nanasaccharides"—Chem. Eur. Journal, vol. 10, (2004), pp. 971-985.
Kajihara, Yasuhiro, et al. —"Convenient Synthesis of a Sialylglycopeptide-thioester Having an Intact and Homogeneous Complex-type Disialyl-Oligosaccharide"—Carbohydrate Research 341 (2006), pp. 1333-1340.

* cited by examiner

*Primary Examiner* — Jeffrey E Russel
(74) *Attorney, Agent, or Firm* — Brinks Hofer Gilson & Lione

(57) ABSTRACT

The present invention provides a process for producing a peptide thioester compound. The process involves: (A) forming a peptide by a solid-phase synthesis method using a resin modified with a linker represented by the formula (1) as a solid phase:

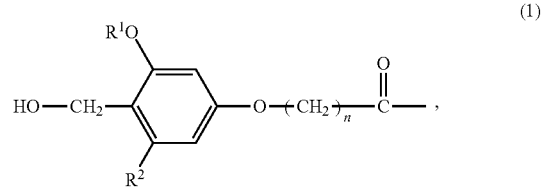

(1)

wherein $R^1$ represents $C_{1-4}$ alkyl group, $R^2$ represents hydrogen atom or $C_{1-4}$ alkoxy group, and n represents an integer of 1 to 4; (B) cleaving a bond between the solid phase and the peptide with at least one acid selected from dilute hydrochloric acid, dilute sulfuric acid, formic acid, and acetic acid to produce a peptide having a carboxyl group at the C-terminus; and (C) reacting a thiol compound with the peptide at −100 to 0° C. in the presence of a condensing agent in a solvent.

21 Claims, No Drawings

```
                       SEQUENCE LISTING

<160> NUMBER OF SEQ ID NOS: 22

<210> SEQ ID NO 1
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Ser having tBu-protected hydroxyl group
<220> FEATURE:
<221> NAME/KEY: MOD_RES
<222> LOCATION: (4)..(4)
<223> OTHER INFORMATION: Ser having tBu-protected hydroxyl group
<220> FEATURE:
<221> NAME/KEY: MOD_RES
<222> LOCATION: (8)..(8)
<223> OTHER INFORMATION: Tyr having tBu-protected hydroxyl group
<220> FEATURE:
<221> NAME/KEY: MOD_RES
<222> LOCATION: (11)..(11)
<223> OTHER INFORMATION: Asp having tBu-protected beta-carboxyl group
<220> FEATURE:
<221> NAME/KEY: MOD_RES
<222> LOCATION: (12)..(12)
<223> OTHER INFORMATION: His having trityl-protected imidazole nitrogen
<220> FEATURE:
<221> NAME/KEY: MOD_RES
<222> LOCATION: (13)..(13)
<223> OTHER INFORMATION: Ser having tBu-protected hyroxyl group
<220> FEATURE:
<221> NAME/KEY: MOD_RES
<222> LOCATION: (14)..(14)
<223> OTHER INFORMATION: His having trityl-protected imidazole nitrogen
<220> FEATURE:
<221> NAME/KEY: MOD_RES
<222> LOCATION: (17)..(17)
<223> OTHER INFORMATION: Tyr having tBu-protected hydroxyl group
<220> FEATURE:
<221> NAME/KEY: MOD_RES
<222> LOCATION: (18)..(18)
<223> OTHER INFORMATION: Tyr having tBu-protected hydroxyl group

<400> SEQUENCE: 1

Asn Ser Val Ser Phe Phe Leu Tyr Asn Leu Asp His Ser His Ala Asn
1               5                   10                  15

Tyr Tyr Phe

<210> SEQ ID NO 2
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: CARBOHYD
<222> LOCATION: (1)..(1)
<223> OTHER INFORMATION: Asn glycosylated by disialo oligosaccharide
      chain
<220> FEATURE:
<221> NAME/KEY: CARBOHYD
```

```
<222> LOCATION: (1)..(1)
<223> OTHER INFORMATION: Asn glycosylated by oligosaccharide chain
<220> FEATURE:
<221> NAME/KEY: MOD_RES
<222> LOCATION: (3)..(3)
<223> OTHER INFORMATION: Ser having tBu-protected hydroxyl group
<220> FEATURE:
<221> NAME/KEY: MOD_RES
<222> LOCATION: (5)..(5)
<223> OTHER INFORMATION: Ser having tBu-protected hydroxyl group
<220> FEATURE:
<221> NAME/KEY: MOD_RES
<222> LOCATION: (9)..(9)
<223> OTHER INFORMATION: Tyr having tBu-protected hydroxyl group
<220> FEATURE:
<221> NAME/KEY: MOD_RES
<222> LOCATION: (12)..(12)
<223> OTHER INFORMATION: Asp having tBu-protected beta-carboxyl group
<220> FEATURE:
<221> NAME/KEY: MOD_RES
<222> LOCATION: (13)..(13)
<223> OTHER INFORMATION: His having trityl-protected imidazole nitrogen
<220> FEATURE:
<221> NAME/KEY: MOD_RES
<222> LOCATION: (14)..(14)
<223> OTHER INFORMATION: Ser having tBu-protected hydroxyl group
<220> FEATURE:
<221> NAME/KEY: MOD_RES
<222> LOCATION: (15)..(15)
<223> OTHER INFORMATION: His having trityl-protected imidazole nitrogen
<220> FEATURE:
<221> NAME/KEY: MOD_RES
<222> LOCATION: (18)..(18)
<223> OTHER INFORMATION: Tyr having tBu-protected hydroxyl group
<220> FEATURE:
<221> NAME/KEY: MOD_RES
<222> LOCATION: (19)..(19)
<223> OTHER INFORMATION: Tyr having tBu-protected hydroxyl group

<400> SEQUENCE: 2

Asn Asn Ser Val Ser Phe Phe Leu Tyr Asn Leu Asp His Ser His Ala
1               5                   10                  15

Asn Tyr Tyr Phe
            20

<210> SEQ ID NO 3
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Cys having Boc-protected amino group and
      acetamidomethyl-protected thiol group
<220> FEATURE:
<221> NAME/KEY: CARBOHYD
<222> LOCATION: (2)..(2)
<223> OTHER INFORMATION: Asn glycosylated by disialo oligosaccharide
      chain
<220> FEATURE:
<221> NAME/KEY: CARBOHYD
<222> LOCATION: (2)..(2)
<223> OTHER INFORMATION: Asn glycosylated by oligosaccharide chain
<220> FEATURE:
<221> NAME/KEY: MOD_RES
<222> LOCATION: (3)..(3)
<223> OTHER INFORMATION: Thr having tBu-protected hydroxyl group
<220> FEATURE:
<221> NAME/KEY: MOD_RES
<222> LOCATION: (4)..(4)
<223> OTHER INFORMATION: Ser having tBu-protected hydroxyl group
<220> FEATURE:
<221> NAME/KEY: MOD_RES
<222> LOCATION: (7)..(7)
<223> OTHER INFORMATION: Thr having tBu-protected hydroxyl group
```

```
<400> SEQUENCE: 3

Cys Asn Thr Ser Val Ile Thr Gln Ala
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Cys having acetamidomethyl-protected thiol
      group
<220> FEATURE:
<221> NAME/KEY: CARBOHYD
<222> LOCATION: (2)..(2)
<223> OTHER INFORMATION: Asn glycosylated by disialo oligosaccharide
      chain
<220> FEATURE:
<221> NAME/KEY: CARBOHYD
<222> LOCATION: (2)..(2)
<223> OTHER INFORMATION: Asn glycosylated by oligosaccharide chain
<220> FEATURE:
<221> NAME/KEY: MOD_RES
<222> LOCATION: (9)..(9)
<223> OTHER INFORMATION: Ala having benzyl thioester group

<400> SEQUENCE: 4

Cys Asn Thr Ser Val Ile Thr Gln Ala
1               5

<210> SEQ ID NO 5
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: His having Ac-protected amino group

<400> SEQUENCE: 5

His Ala Ala Phe
1

<210> SEQ ID NO 6
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: His having Ac-protected amino group
<220> FEATURE:
<221> NAME/KEY: MOD_RES
<222> LOCATION: (4)..(4)
<223> OTHER INFORMATION: Phe having benzyl thioester group

<400> SEQUENCE: 6

His Ala Ala Phe
1

<210> SEQ ID NO 7
<211> LENGTH: 4
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Cys having Ac-protected amino group

<400> SEQUENCE: 7

Cys Cys Glu His
1

<210> SEQ ID NO 8
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Cys having Ac-protected amino group
<220> FEATURE:
<221> NAME/KEY: MOD_RES
<222> LOCATION: (4)..(4)
<223> OTHER INFORMATION: His having benzyl thioester group

<400> SEQUENCE: 8

Cys Cys Glu His
1

<210> SEQ ID NO 9
<211> LENGTH: 23
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Leu having Boc-protected amino group
<220> FEATURE:
<221> NAME/KEY: MOD_RES
<222> LOCATION: (5)..(5)
<223> OTHER INFORMATION: Ser having tBu-protected hydroxyl group
<220> FEATURE:
<221> NAME/KEY: MOD_RES
<222> LOCATION: (7)..(7)
<223> OTHER INFORMATION: Asp having tBu-protected beta-carboxyl group
<220> FEATURE:
<221> NAME/KEY: MOD_RES
<222> LOCATION: (8)..(8)
<223> OTHER INFORMATION: Cys having trityl-protected thiol group
<220> FEATURE:
<221> NAME/KEY: MOD_RES
<222> LOCATION: (9)..(9)
<223> OTHER INFORMATION: Ser having tBu-protected hydroxyl group
<220> FEATURE:
<221> NAME/KEY: MOD_RES
<222> LOCATION: (10)..(10)
<223> OTHER INFORMATION: Glu having tBu-protected gamma-carboxyl group
<220> FEATURE:
<221> NAME/KEY: MOD_RES
<222> LOCATION: (11)..(11)
<223> OTHER INFORMATION: Tyr having tBu-protected hydroxyl group
<220> FEATURE:
<221> NAME/KEY: MOD_RES
<222> LOCATION: (13)..(13)
<223> OTHER INFORMATION: Lys having Boc-protected epsilon-amino group
<220> FEATURE:
<221> NAME/KEY: MOD_RES
<222> LOCATION: (16)..(16)
<223> OTHER INFORMATION: Cys having trityl-protected thiol group
<220> FEATURE:
<221> NAME/KEY: MOD_RES
<222> LOCATION: (17)..(17)
<223> OTHER INFORMATION: Thr having tBu-protected hydroxyl group
```

```
<220> FEATURE:
<221> NAME/KEY: MOD_RES
<222> LOCATION: (19)..(19)
<223> OTHER INFORMATION: Glu having tBu-protected gamma-carboxyl group
<220> FEATURE:
<221> NAME/KEY: MOD_RES
<222> LOCATION: (20)..(20)
<223> OTHER INFORMATION: Tyr having tBu-protected hydroxyl group
<220> FEATURE:
<221> NAME/KEY: MOD_RES
<222> LOCATION: (21)..(21)
<223> OTHER INFORMATION: Arg having Pbf-protected guanidine nitrogen

<400> SEQUENCE: 9

Leu Ala Ala Val Ser Val Asp Cys Ser Glu Tyr Pro Lys Pro Ala Cys
1               5                   10                  15

Thr Met Glu Tyr Arg Pro Leu
            20

<210> SEQ ID NO 10
<211> LENGTH: 23
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (23)..(23)
<223> OTHER INFORMATION: Leu having benzyl thioester group

<400> SEQUENCE: 10

Leu Ala Ala Val Ser Val Asp Cys Ser Glu Tyr Pro Lys Pro Ala Cys
1               5                   10                  15

Thr Met Glu Tyr Arg Pro Leu
            20

<210> SEQ ID NO 11
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Glu having tBu-protected gamma-carboxyl group
<220> FEATURE:
<221> NAME/KEY: MOD_RES
<222> LOCATION: (2)..(2)
<223> OTHER INFORMATION: Tyr having tBu-protected hydroxyl group
<220> FEATURE:
<221> NAME/KEY: MOD_RES
<222> LOCATION: (4)..(4)
<223> OTHER INFORMATION: Ser having tBu-protected hydroxyl group
<220> FEATURE:
<221> NAME/KEY: MOD_RES
<222> LOCATION: (7)..(7)
<223> OTHER INFORMATION: Lys having Boc-protected epsilon-amino group
<220> FEATURE:
<221> NAME/KEY: MOD_RES
<222> LOCATION: (9)..(9)
<223> OTHER INFORMATION: Thr having tBu-protected hydroxyl group
<220> FEATURE:
<221> NAME/KEY: MOD_RES
<222> LOCATION: (10)..(10)
<223> OTHER INFORMATION: Glu having tBu-protected gamma-carboxyl group
<220> FEATURE:
<221> NAME/KEY: MOD_RES
<222> LOCATION: (12)..(12)
<223> OTHER INFORMATION: Arg having Pbf-protected guanidine nitrogen
<220> FEATURE:
<221> NAME/KEY: MOD_RES
<222> LOCATION: (14)..(14)
<223> OTHER INFORMATION: Thr having tBu-protected hydroxyl group
```

```
<220> FEATURE:
<221> NAME/KEY: MOD_RES
<222> LOCATION: (17)..(17)
<223> OTHER INFORMATION: Arg having Pbf-protected guanidine nitrogen
<220> FEATURE:
<221> NAME/KEY: MOD_RES
<222> LOCATION: (18)..(18)
<223> OTHER INFORMATION: Gln having trityl-protected amide nitrogen
<220> FEATURE:
<221> NAME/KEY: MOD_RES
<222> LOCATION: (20)..(20)
<223> OTHER INFORMATION: Asp having tBu-protected beta-carboxyl group
<220> FEATURE:
<221> NAME/KEY: MOD_RES
<222> LOCATION: (21)..(21)
<223> OTHER INFORMATION: Ser having tBu-protected hydroxyl group
<220> FEATURE:
<221> NAME/KEY: MOD_RES
<222> LOCATION: (22)..(22)
<223> OTHER INFORMATION: Gln having trityl-protected amide nitrogen
<220> FEATURE:
<221> NAME/KEY: MOD_RES
<222> LOCATION: (24)..(24)
<223> OTHER INFORMATION: Thr having tBu-protected hydroxyl group
<220> FEATURE:
<221> NAME/KEY: MOD_RES
<222> LOCATION: (25)..(25)
<223> OTHER INFORMATION: Glu having tBu-protected gamma-carboxyl group

<400> SEQUENCE: 11

Glu Tyr Ala Ser Pro Gly Lys Ala Thr Glu Val Arg Val Thr Val Leu
1               5                   10                  15

Arg Gln Ala Asp Ser Gln Val Thr Glu Gly
            20                  25

<210> SEQ ID NO 12
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: 1,3-thiazolidine-4-carbonyl
<220> FEATURE:
<221> NAME/KEY: MOD_RES
<222> LOCATION: (2)..(2)
<223> OTHER INFORMATION: Glu having tBu-proteced gamma-carboxyl group
<220> FEATURE:
<221> NAME/KEY: MOD_RES
<222> LOCATION: (3)..(3)
<223> OTHER INFORMATION: Tyr having tBu-protected hydroxyl group
<220> FEATURE:
<221> NAME/KEY: MOD_RES
<222> LOCATION: (5)..(5)
<223> OTHER INFORMATION: Ser having tBu-protected hydroxyl group
<220> FEATURE:
<221> NAME/KEY: MOD_RES
<222> LOCATION: (8)..(8)
<223> OTHER INFORMATION: Lys having Boc-protected epsilon-amino group
<220> FEATURE:
<221> NAME/KEY: MOD_RES
<222> LOCATION: (10)..(10)
<223> OTHER INFORMATION: Thr having tBu-protected hydroxyl group
<220> FEATURE:
<221> NAME/KEY: MOD_RES
<222> LOCATION: (11)..(11)
<223> OTHER INFORMATION: Glu having tBu-protected gamma-carboxyl group
<220> FEATURE:
<221> NAME/KEY: MOD_RES
<222> LOCATION: (13)..(13)
<223> OTHER INFORMATION: Arg having Pbf-protected guanidine nitrogen
<220> FEATURE:
<221> NAME/KEY: MOD_RES
<222> LOCATION: (15)..(15)
<223> OTHER INFORMATION: Thr having tBu-protected hydroxyl group
```

```
<220> FEATURE:
<221> NAME/KEY: MOD_RES
<222> LOCATION: (18)..(18)
<223> OTHER INFORMATION: Arg having Pbf-protected guanidine nitrogen
<220> FEATURE:
<221> NAME/KEY: MOD_RES
<222> LOCATION: (19)..(19)
<223> OTHER INFORMATION: Gln having trityl-protected amide nitrogen
<220> FEATURE:
<221> NAME/KEY: MOD_RES
<222> LOCATION: (21)..(21)
<223> OTHER INFORMATION: Asp having tBu-protected beta-carboxyl group
<220> FEATURE:
<221> NAME/KEY: MOD_RES
<222> LOCATION: (22)..(22)
<223> OTHER INFORMATION: Ser having tBu-protected hydroxyl group
<220> FEATURE:
<221> NAME/KEY: MOD_RES
<222> LOCATION: (23)..(23)
<223> OTHER INFORMATION: Gln having trityl-protected amide nitrogen
<220> FEATURE:
<221> NAME/KEY: MOD_RES
<222> LOCATION: (25)..(25)
<223> OTHER INFORMATION: Thr having tBu-protected hydroxyl group
<220> FEATURE:
<221> NAME/KEY: MOD_RES
<222> LOCATION: (26)..(26)
<223> OTHER INFORMATION: Glu having tBu-protected gamma-carboxyl group

<400> SEQUENCE: 12

Xaa Glu Tyr Ala Ser Pro Gly Lys Ala Thr Glu Val Arg Val Thr Val
1               5                   10                  15

Leu Arg Gln Ala Asp Ser Gln Val Thr Glu Gly
            20                  25

<210> SEQ ID NO 13
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: 1,3-thiazolidine-4-carbonyl
<220> FEATURE:
<221> NAME/KEY: MOD_RES
<222> LOCATION: (27)..(27)
<223> OTHER INFORMATION: Gly having benzyl thioester group

<400> SEQUENCE: 13

Xaa Glu Tyr Ala Ser Pro Gly Lys Ala Thr Glu Val Arg Val Thr Val
1               5                   10                  15

Leu Arg Gln Ala Asp Ser Gln Val Thr Glu Gly
            20                  25

<210> SEQ ID NO 14
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Thr having tBu-protected hydroxyl group
<220> FEATURE:
<221> NAME/KEY: MOD_RES
<222> LOCATION: (4)..(4)
<223> OTHER INFORMATION: Tyr having tBu-protected hydroxyl group
<220> FEATURE:
<221> NAME/KEY: MOD_RES
<222> LOCATION: (9)..(9)
<223> OTHER INFORMATION: Glu having tBu-protected gamma-carboxyl group
```

```
<220> FEATURE:
<221> NAME/KEY: MOD_RES
<222> LOCATION: (11)..(11)
<223> OTHER INFORMATION: Thr having tBu-protected hydroxyl group
<220> FEATURE:
<221> NAME/KEY: MOD_RES
<222> LOCATION: (14)..(14)
<223> OTHER INFORMATION: Asp having tBu-protected beta-carboxyl group
<220> FEATURE:
<221> NAME/KEY: MOD_RES
<222> LOCATION: (15)..(15)
<223> OTHER INFORMATION: Asp having tBu-protected beta-carboxyl group
<220> FEATURE:
<221> NAME/KEY: MOD_RES
<222> LOCATION: (16)..(16)
<223> OTHER INFORMATION: Ser having tBu-protected hydroxyl group

<400> SEQUENCE: 14

Ala Ala Thr Tyr Met Met Gly Asn Glu Leu Thr Phe Leu Asp Asp Ser
1               5                   10                  15

Gly

<210> SEQ ID NO 15
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: 1,3-thiazolidine-4-carbonyl
<220> FEATURE:
<221> NAME/KEY: MOD_RES
<222> LOCATION: (4)..(4)
<223> OTHER INFORMATION: Thr having tBu-protected hydroxyl group
<220> FEATURE:
<221> NAME/KEY: MOD_RES
<222> LOCATION: (5)..(5)
<223> OTHER INFORMATION: Tyr having tBu-protected hydroxyl group
<220> FEATURE:
<221> NAME/KEY: MOD_RES
<222> LOCATION: (10)..(10)
<223> OTHER INFORMATION: Glu having tBu-protected gamma-carboxyl group
<220> FEATURE:
<221> NAME/KEY: MOD_RES
<222> LOCATION: (12)..(12)
<223> OTHER INFORMATION: Thr having tBu-protected hydroxyl group
<220> FEATURE:
<221> NAME/KEY: MOD_RES
<222> LOCATION: (15)..(15)
<223> OTHER INFORMATION: Asp having tBu-protected beta-carboxyl group
<220> FEATURE:
<221> NAME/KEY: MOD_RES
<222> LOCATION: (16)..(16)
<223> OTHER INFORMATION: Asp having tBu-protected beta-carboxyl group
<220> FEATURE:
<221> NAME/KEY: MOD_RES
<222> LOCATION: (17)..(17)
<223> OTHER INFORMATION: Ser having tBu-protected hydroxyl group

<400> SEQUENCE: 15

Xaa Ala Ala Thr Tyr Met Met Gly Asn Glu Leu Thr Phe Leu Asp Asp
1               5                   10                  15

Ser Gly

<210> SEQ ID NO 16
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
```

```
<222> LOCATION: (1)..(1)
<223> OTHER INFORMATION: 1,3-thiazolidine-4-carbonyl
<220> FEATURE:
<221> NAME/KEY: MOD_RES
<222> LOCATION: (18)..(18)
<223> OTHER INFORMATION: Gly having benzyl thioester group

<400> SEQUENCE: 16

Xaa Ala Ala Thr Tyr Met Met Gly Asn Glu Leu Thr Phe Leu Asp Asp
1               5                   10                  15

Ser Gly

<210> SEQ ID NO 17
<211> LENGTH: 22
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Lys having Box-protected alpha- and
      epsilon-amino groups
<220> FEATURE:
<221> NAME/KEY: MOD_RES
<222> LOCATION: (4)..(4)
<223> OTHER INFORMATION: His having trityl-protected imidazole nitrogen
<220> FEATURE:
<221> NAME/KEY: MOD_RES
<222> LOCATION: (7)..(7)
<223> OTHER INFORMATION: Gln having trityl-protected amide nitrogen
<220> FEATURE:
<221> NAME/KEY: MOD_RES
<222> LOCATION: (14)..(14)
<223> OTHER INFORMATION: Ser having tBu-protected hydroxyl group
<220> FEATURE:
<221> NAME/KEY: MOD_RES
<222> LOCATION: (15)..(15)
<223> OTHER INFORMATION: Ser having tBu-protected hydroxyl group
<220> FEATURE:
<221> NAME/KEY: MOD_RES
<222> LOCATION: (16)..(16)
<223> OTHER INFORMATION: Arg having Pbf-protected guanidine nitrogen
<220> FEATURE:
<221> NAME/KEY: MOD_RES
<222> LOCATION: (20)..(20)
<223> OTHER INFORMATION: Ser having tBu-protected hydroxyl group

<400> SEQUENCE: 17

Lys Ala Met His Val Ala Gln Pro Ala Val Val Leu Ala Ser Ser Arg
1               5                   10                  15

Gly Ile Ala Ser Phe Gly
            20

<210> SEQ ID NO 18
<211> LENGTH: 22
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (22)..(22)
<223> OTHER INFORMATION: Gly having benzyl thioester group

<400> SEQUENCE: 18

Lys Ala Met His Val Ala Gln Pro Ala Val Val Leu Ala Ser Ser Arg
1               5                   10                  15

Gly Ile Ala Ser Phe Gly
            20
```

```
<210> SEQ ID NO 19
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Lys having Boc-protected epsilon-amino group
<220> FEATURE:
<221> NAME/KEY: MOD_RES
<222> LOCATION: (2)..(2)
<223> OTHER INFORMATION: Thr having tBu-protected hydroxyl group
<220> FEATURE:
<221> NAME/KEY: MOD_RES
<222> LOCATION: (3)..(3)
<223> OTHER INFORMATION: Tyr having tBu-protected hydroxyl group
<220> FEATURE:
<221> NAME/KEY: MOD_RES
<222> LOCATION: (6)..(6)
<223> OTHER INFORMATION: Lys having Boc-protected epsilon-amino group
<220> FEATURE:
<221> NAME/KEY: MOD_RES
<222> LOCATION: (7)..(7)
<223> OTHER INFORMATION: Cys having trityl-protected thiol group

<400> SEQUENCE: 19

Lys Thr Tyr Gly Asn Lys Cys Asn Phe
1               5

<210> SEQ ID NO 20
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: CARBOHYD
<222> LOCATION: (1)..(1)
<223> OTHER INFORMATION: Asn glycosylated by oligosaccharide chain
<220> FEATURE:
<221> NAME/KEY: MOD_RES
<222> LOCATION: (2)..(2)
<223> OTHER INFORMATION: Lys having Boc-protected epsilon-amino group
<220> FEATURE:
<221> NAME/KEY: MOD_RES
<222> LOCATION: (3)..(3)
<223> OTHER INFORMATION: Thr having tBu-protected hydroxyl group
<220> FEATURE:
<221> NAME/KEY: MOD_RES
<222> LOCATION: (4)..(4)
<223> OTHER INFORMATION: Tyr having tBu-protected hydroxyl group
<220> FEATURE:
<221> NAME/KEY: MOD_RES
<222> LOCATION: (7)..(7)
<223> OTHER INFORMATION: Lys having Boc-protected epsilon-amino group
<220> FEATURE:
<221> NAME/KEY: MOD_RES
<222> LOCATION: (8)..(8)
<223> OTHER INFORMATION: Cys having trityl-protected thiol group

<400> SEQUENCE: 20

Asn Lys Thr Tyr Gly Asn Lys Cys Asn Phe
1               5                   10

<210> SEQ ID NO 21
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: 1,3-thiazolidine-4-carbonyl
```

```
<220> FEATURE:
<221> NAME/KEY: MOD_RES
<222> LOCATION: (3)..(3)
<223> OTHER INFORMATION: Ser having tBu-protected hydroxyl group
<220> FEATURE:
<221> NAME/KEY: CARBOHYD
<222> LOCATION: (5)..(5)
<223> OTHER INFORMATION: Asn glycosylated by oligosaccharide chain
<220> FEATURE:
<221> NAME/KEY: MOD_RES
<222> LOCATION: (6)..(6)
<223> OTHER INFORMATION: Lys having Boc-protected epsilon-amino group
<220> FEATURE:
<221> NAME/KEY: MOD_RES
<222> LOCATION: (7)..(7)
<223> OTHER INFORMATION: Thr having tBu-protected hydroxyl group
<220> FEATURE:
<221> NAME/KEY: MOD_RES
<222> LOCATION: (8)..(8)
<223> OTHER INFORMATION: Tyr having tBu-protected hydroxyl group
<220> FEATURE:
<221> NAME/KEY: MOD_RES
<222> LOCATION: (11)..(11)
<223> OTHER INFORMATION: Lys having Boc-protected epsilon-amino group
<220> FEATURE:
<221> NAME/KEY: MOD_RES
<222> LOCATION: (12)..(12)
<223> OTHER INFORMATION: Cys having trityl-protected thiol group

<400> SEQUENCE: 21

Xaa Gly Ser Asp Asn Lys Thr Tyr Gly Asn Lys Cys Asn Phe
1               5                   10

<210> SEQ ID NO 22
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: 1,3-thiazolidine-4-carbonyl
<220> FEATURE:
<221> NAME/KEY: CARBOHYD
<222> LOCATION: (5)..(5)
<223> OTHER INFORMATION: Asn glycosylated by oligosaccharide chain
<220> FEATURE:
<221> NAME/KEY: MOD_RES
<222> LOCATION: (14)..(14)
<223> OTHER INFORMATION: Phe having benzyl thioester group

<400> SEQUENCE: 22

Xaa Gly Ser Asp Asn Lys Thr Tyr Gly Asn Lys Cys Asn Phe
1               5                   10
```

METHOD FOR PRODUCTION OF PEPTIDE THIOESTER COMPOUND

TECHNICAL FIELD

The present invention relates to a process for producing a peptide thioester compound.

BACKGROUND ART

Many proteins existing in vivo are glycoproteins, proteins having oligosaccharide chains. Oligosaccharide chains in glycoproteins work in such a way that they maintain the three-dimensional structures of the proteins, regulate solubility, and impart protease resistance thereto. It is now becoming evident that the oligosaccharide chains in glycoproteins are involved in life phenomena such as fertilization or differentiation, signal transduction, canceration, intracellular protein transport, and regulation of biological activities. Thus, oligosaccharide chains bonded to proteins play an important role in various physiological functions. However, these oligosaccharide chains have diverse structures, and they are classified into various categories. Under the circumstances, it is therefore extremely difficult to identify which oligosaccharide chain structure is involved in a life phenomenon. Synthesis of glycoproteins or glycopeptides having an oligosaccharide chain with a single structure is also indispensable for elucidating such functions. At present, glycoproteins can be expressed by biological approaches using protein expression, although glycoproteins having an oligosaccharide chain with a uniform structure are difficult to obtain. Therefore, studies have been made in recent years on the precise chemical synthesis of glycopeptides or glycoproteins having an oligosaccharide chain with a single structure.

The present inventors have established a process for preparing a large amount of a biantennary complex-type oligosaccharide chain that can be used as a raw material from a chicken egg by combining enzymatic and chemical methods (Patent Document 1) and a process for synthesizing a sialylated glycopeptide by applying a solid-phase peptide synthesis method to a complex-type oligosaccharide chain (Patent Document 2). If glycopeptides can be polymerized, large glycoproteins having an oligosaccharide chain with a single structure will be synthesized.

At present, the most effective peptide polymerization method is probably the native chemical ligation method (Non-Patent Document 1), which involves coupling a peptide fragment having cysteine (Cys) as an N-terminal amino acid to a peptide having thioester at the C-terminus.

Peptide synthesis methods generally used are solid-phase synthesis methods, which involve immobilizing an N-terminal protected amino acid onto an insoluble resin support, removing the protecting group in the amino acid, and then sequentially elongating a peptide chain. Examples of a method for producing the peptide having thioester at the C-terminus include a method which involves performing thioesterification during peptide excision from a solid phase and a method which involves subjecting the C-terminal carboxyl group of a peptide to thioesterification after peptide excision from a solid phase.

For example, a method which involves producing a peptide using a safety catch linker on a solid-phase resin and allowing a thiol compound to act thereon (Non-Patent Documents 1 and 2) is known as a method for performing the thioesterification during peptide excision from a solid phase. However, this method has many problems such as poor condensation efficiency in the immobilization of a first amino acid onto a resin, the slight racemization of amino acids during the condensation, and the poor reactivity of the thiol compound in esterification. Moreover, when a hydroxyl group of an oligosaccharide chain in a glycopeptide is unprotected, alkylation performed for activating the safety catch linker also alkylates the sugar hydroxyl group easily. Thus, dealkylation treatment must be performed. This treatment may influence glycosylation and so on, depending on conditions, and a uniform oligosaccharide chain structure cannot be secured in the obtained glycopeptide. To solve this problem, it is suggested that the hydroxyl group of the oligosaccharide chain is protected in advance. However, this approach is not efficient due to additional protection and deprotection steps.

A strong acid such as 95% trifluoroacetic acid or hydrogen fluoride is usually used for excising a peptide from a solid-phase resin. However, the use of such a strong acid involves the deprotection of peptide side chains or the cleavage of an oligosaccharide chain linkage in glycopeptides. A method using a trityl resin as a solid phase and acetic acid for excision (Non-Patent Documents 3, 4, and 5) and a method using a 4-hydroxymethyl-3-methoxyphenoxybutyric acid-modified resin (HMPB resin) as a solid phase and 1% trifluoroacetic acid (TFA) for excision (Non-Patent Document 6) have been reported as methods for excising a peptide from a solid-phase resin using a weak acid without causing deprotection. However, the method using a trityl resin cannot produce glycopeptides having an unprotected hydroxyl group. On the other hand, when a glycopeptide is prepared using the HMPB resin as a solid phase, the use of 1% TFA cannot excise the glycopeptide. Alternatively, the use of 10% TFA also causes the partial removal of protecting groups in the peptide side chains. For peptide thioesterification, particularly, the protection of the thiol group of N-terminal cysteine is essential for preventing self-condensation. Thus, deprotection during excision leads to fatal outcomes. Accordingly, these methods are not sufficient for producing a peptide having a carboxyl group, which is used as a raw material in the production of a peptide having thioester at the C-terminus.

A thioester form of a peptide can be produced by reacting a peptide having protected side chains with alkylthiol. However, this approach has the problem of C-terminal amino acid racemization. For circumventing racemization, a method which involves replacing a C-terminal amino acid by glycine (Non-Patent Document 7), a method using benzotriazol-1-yloxy-trispyrrolidinophosphonium hexafluorophosphate (PyBOP)/diisopropylethylamine (DIPEA) as a condensing agent in dichloromethane (DCM) (Non-Patent Document 8), and a method using 2-(1H-benzotriazol-1-yl)-1,1,3,3-tetramethyluronium hexafluorophosphate (HBTU)/DIPEA as a condensing agent in tetrahydrofuran (THF) (Non-Patent Document 9) have been reported. However, the method which involves replacing a C-terminal amino acid by glycine has a natural limit to the types of peptides that can be produced. Moreover, glycopeptides having a hydroxyl group that is not protected with a protecting group cannot be dissolved in the solvent such as DCM or THF. Thus, these solvents must be changed, although the C-terminal amino acid racemization becomes a problem again.

[Patent Document 1] WO 03/008431
[Patent Document 2] WO 2004/005330
[Non-Patent Document 1] J. Am. Chem. Soc., 121, 11369-11374 (1999)
[Non-Patent Document 2] Angew. Chem. Int. Ed., 44, 1650-1654 (2005)
[Non-Patent Document 3] Tetrahedron Lett., 38, 6237-6240 (1997)
[Non-Patent Document 4] Tetrahedron Lett., 44, 3551-3554 (2003)
[Non-Patent Document 5] J. Am. Chem. Soc., 123, 3885-3891 (2001)
[Non-Patent Document 6] Tetrahedron, 49, 9307-9320 (1993)

[Non-Patent Document 7] Tetrahedron Lett., 38, 6237-6240 (1997)

[Non-Patent Document 8] Tetrahedron Lett., 44, 3551-3554 (2003)

[Non-Patent Document 9] J. Am. Chem. Soc., 123, 3885-3891 (2001)

An object of the present invention is to provide a process for producing a peptide having a carboxyl group at the C-terminus, with protecting groups in the peptide side chains maintained, which is applicable to a non-glycosylated peptide or even to a glycopeptide having an oligosaccharide chain, particularly, an oligosaccharide chain with an unprotected hydroxyl group.

Another object of the present invention is to provide a process for efficiently producing a peptide thioester compound, with racemization reduced, which is applicable to a non-glycosylated peptide or even to a glycopeptide having an oligosaccharide chain, particularly, an oligosaccharide chain with an unprotected hydroxyl group.

DISCLOSURE OF THE INVENTION

The present invention relates to the following invention:

a process for producing a peptide thioester compound, characterized by comprising:

(A) forming a peptide by a solid-phase synthesis method using a resin modified with a linker represented by the formula (1) as a solid phase;

(B) cleaving a bond between the solid phase and the peptide with at least one acid selected from dilute hydrochloric acid, dilute sulfuric acid, formic acid, and acetic acid to produce a peptide having a carboxyl group at the C-terminus; and (C) reacting a thiol compound with the peptide at −100 to 0° C. in the presence of a condensing agent in a solvent:

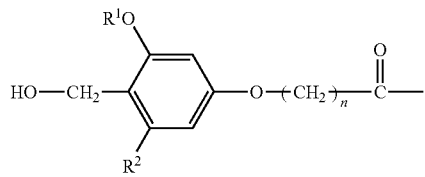

(1)

wherein $R^1$ represents a $C_{1-4}$ alkyl group, $R^2$ represents a hydrogen atom or $C_{1-4}$ alkoxy group, and n represents an integer of 1 to 4.

The present inventors have found that a peptide produced under particular conditions using a particular solid-phase resin can be excised from the solid-phase resin to thereby produce a peptide having a carboxyl group at the C-terminus, with protecting groups in the side chains maintained, without influencing the oligosaccharide chain structure.

The present inventors have further found that a thiol compound can be allowed to act on the C-terminal carboxyl group of the obtained peptide at a low temperature in the presence of a particular condensing agent to thereby produce a peptide thioester compound, with the C-terminal racemization of the peptide reduced.

The process for producing a peptide thioester compound according to the present invention comprises the steps of: (A) forming a peptide by a solid-phase synthesis method using a resin modified with a linker represented by the formula (1) as a solid phase; (B) cleaving the bond between the solid phase and the peptide with at least one acid selected from dilute hydrochloric acid, dilute sulfuric acid, formic acid, and acetic acid to produce a peptide having a carboxyl group at the C-terminus; and (C) reacting a thiol compound with the peptide at −100 to 0° C. in the presence of a condensing agent in a solvent.

Step (A): Peptide Formation

In this step, a resin modified with a linker represented by the formula (1) is used:

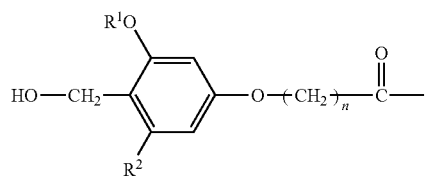

(1)

wherein $R^1$ represents $C_{1-4}$ alkyl group, $R^2$ represents hydrogen atom or $C_{1-4}$ alkoxy group, and n represents an integer of 1 to 4.

The $C_{1-4}$ alkyl group refers to linear or branched alkyl groups having 1 to 4 carbon atoms, such as methyl, ethyl, n-propyl, isopropyl, n-butyl, isobutyl, sec-butyl, and tert-butyl groups.

The $C_{1-4}$ alkoxy group refers to linear or branched alkoxy groups having 1 to 4 carbon atoms, such as methoxy, ethoxy, n-propoxy, isopropoxy, n-butoxy, isobutoxy, sec-butoxy, and tert-butoxy groups.

The resin modified with a linker represented by the formula (1) may be a commercially available resin or a resin previously known in the art. Examples thereof include HMPB-BHA (4-hydroxymethyl-3-methoxyphenoxybutyric acid-benzhydrylamine) and HMPB-MBHA (4-hydroxymethyl-3-methoxyphenoxybutyric acid-methylbenzhydrylamine) resins. In glycopeptide production, a highly swellable resin can be used, which is obtained by reacting the amino group of an amino-PEGA resin (manufactured by Novabiochem) with the carboxyl group of a carboxylic acid compound represented by the formula (2) in the presence of a dehydration condensing agent according to amidation reaction previously known in the art (in this context, PEGA resin refers to bisacrylamidoprop-1-yl polyethyleneglycol):

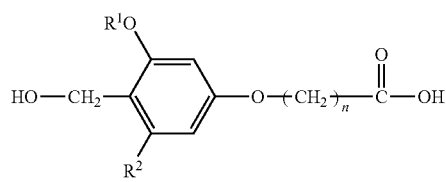

(2)

wherein $R^1$, $R^2$, and n are the same as above.

Among the obtained resins having the linker represented by the formula (1), a resin wherein $R^1$ is a methyl group and $R^2$ is a hydrogen atom or $C_{1-4}$ alkyl group is preferable. A resin wherein $R^1$ is a methyl group, $R^2$ is a hydrogen atom or $C_{1-4}$ alkyl group, and n is an integer of 2 to 4 is more preferable. A resin wherein $R^1$ is a methyl group, $R^2$ is a hydrogen atom or $C_{1-4}$ alkyl group, and n is 3 is particularly preferable.

Specifically, for example, a resin represented by the formula (3) is particularly preferable:

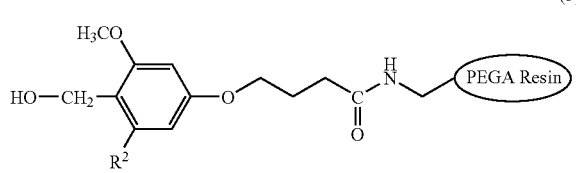

(3)

wherein $R^2$ is the same as above.

The resin modified with a linker represented by the formula (1) is used as a solid phase for peptide production.

Examples of steps of the peptide production include the following steps (a) to (e):

(a) reacting, through esterification, the hydroxyl group of the linker moiety represented by the formula (1) in the resin modified with the linker represented by the formula (1) with the carboxyl group of an amino acid having an amino group protected with a protecting group;

(b) removing the protecting group in the amino group to form an unprotected amino group;

(c) reacting, through amidation, this unprotected amino group with the carboxyl group of an amino acid having a protected amino group;

(d) removing the protecting group to form an unprotected amino group; and (e) repeating the steps (c) and (d) at least once to form a peptide.

All amino acids can be used as the amino acids described above. Examples thereof can include serine (Ser), asparagine (Asn), valine (Val), leucine (Leu), isoleucine (Ile), alanine (Ala), tyrosine (Tyr), glycine (Gly), lysine (Lys), arginine (Arg), histidine (His), aspartic acid (Asp), glutamic acid (Glu), glutamine (Gln), threonine (Thr), cysteine (Cys), methionine (Met), phenylalanine (Phe), tryptophan (Trp), and proline (Pro).

Examples of the protecting group can include protecting groups such as 9-fluorenylmethyloxycarbonyl (Fmoc), t-butyloxycarbonyl (Boc), carbonate-containing (e.g., allyloxycarbonate (Alloc)), acyl (e.g., acetyl), allyl, and benzyl groups. To introduce the protecting group, for example, the Fmoc group can be introduced by performing reaction by the addition of 9-fluorenylmethyl-N-succinimidyl carbonate and sodium hydrogen carbonate. The reaction may be performed at 0 to 50° C., preferably at room temperature, for approximately 1 to 5 hours.

An amino acid having an amino group protected with a fat-soluble protecting group can be produced by introducing a fat-soluble protecting group to the amino group of the amino acid according to the method described above or a method known in the art. Alternatively, those commercially available can also be used. Examples of an amino acid having an amino group protected with an Fmoc group can include Fmoc-Ser, Fmoc-Asn, Fmoc-Val, Fmoc-Leu, Fmoc-Ile, Fmoc-Ala, Fmoc-Tyr, Fmoc-Gly, Fmoc-Lys, Fmoc-Arg, Fmoc-His, Fmoc-Asp, Fmoc-Glu, Fmoc-Gln, Fmoc-Thr, Fmoc-Cys, Fmoc-Met, Fmoc-Phe, Fmoc-Trp, Fmoc-Pro.

Cysteine (Cys) can be selected as an amino acid to be introduced finally to thereby produce a peptide having cysteine at the N-terminus. This peptide can be used as a fragment to be coupled with a peptide thiol ester compound in native chemical ligation.

A glycosylated amino acid in which an oligosaccharide chain is bonded to an amino acid can be used to thereby produce a glycopeptide having the glycosylated amino acid introduced at an arbitrary position in the peptide chain.

The glycosylated amino acid used is not particularly limited as long as it has any number of sugar residues. Examples thereof can include a high-mannose-type oligosaccharide chain rich in mannose, a complex-type oligosaccharide chain having a sialic acid or galactose residue at the oligosaccharide chain nonreducing end (FIG. 1), a hybrid-type oligosaccharide chain comprising a high-mannose structure mixed with a complex-type oligosaccharide chain, an N-linked oligosaccharide chain in which asparagine is N-glycosylated on its side chain amide group, and an O-linked oligosaccharide chain in which an alcohol in a serine or threonine side chain is glycosylated. Specific examples thereof can include glycosylated asparagine described in WO 03/008431. Among them, disialo- or monosialo-oligosaccharide chain added asparagine is preferable. For example, an oligosaccharide chain having a carboxyl group of the sialic acid protected with a protecting group such as a benzyl group is particularly preferable, which is represented by the formula (4). A glycopeptide comprising such disialo- or monosialo-oligosaccharide chain added asparagine bonded thereto is a preferable glycopeptide.

(4)

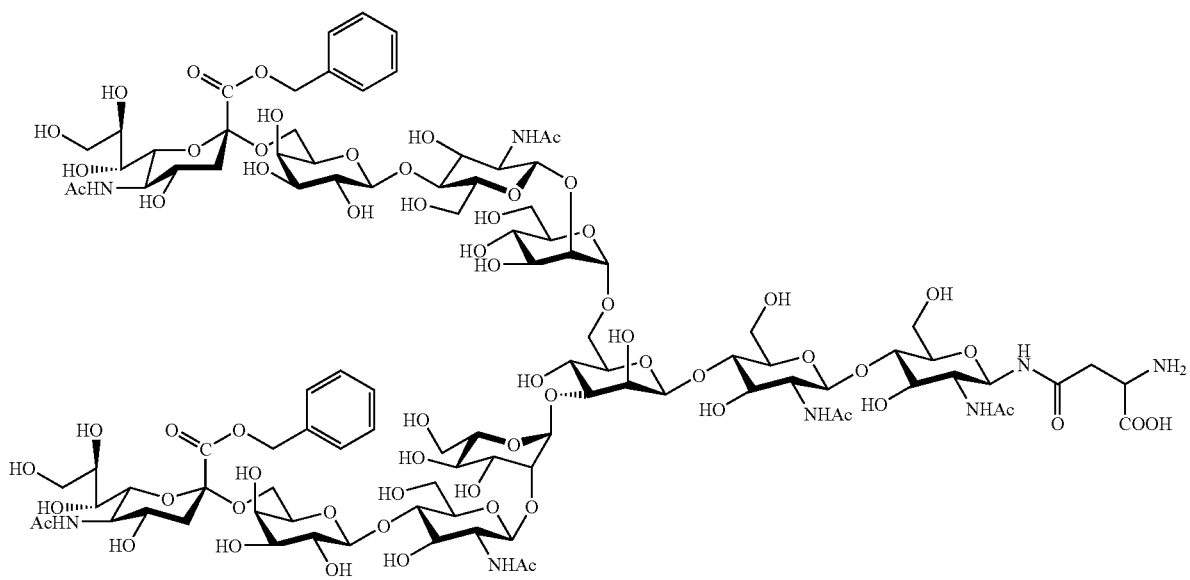

The esterification reaction of the hydroxyl group of the linker moiety in the resin with the carboxyl group of the amino acid having a protected amino group can be performed using, for example, a dehydration condensing agent such as 1-mesitylenesulfonyl-3-nitro-1,2,4-triazole (MSNT), DCC, or diisopropylcarbodiimide (DIPCDI) and is preferably performed, for example, by placing the resin in a solid-phase column, washing the resin with a solvent, and then adding a solvent solution of the amino acid thereto.

Examples of the solvent for washing can include DMF, 2-propanol, and DCM. Examples of the solvent for dissolving the amino acid therein can include DMSO, DMF, and DCM. The reaction may be performed at 0 to 50° C., preferably at room temperature, for approximately 10 minutes to 30 hours, preferably for approximately 15 minutes to 24 hours.

In this procedure, unreacted hydroxyl groups on the solid phase may also be acetylated for capping using an acetic anhydride or the like.

The removal of the protecting group in the amino group can be performed by treatment with an acid or base. For example, when the protecting group is an Fmoc group, a base such as piperidine or morpholine can be used. This procedure is preferably performed in the presence of a solvent. Examples of the solvent can include DMSO, DMF, and methanol.

The amidation reaction of the unprotected amino group with the carboxyl group of any amino acid having a protected amino group is preferably performed in the presence of an activator and a solvent.

Examples of the activator can include dicyclohexylcarbodiimide (DCC), 1-ethyl-3-(3-dimethylaminopropyl)carbodiimide.hydrochloride (WSC/HCl), diphenylphosphoryl azide (DPPA), carbonyldiimidazole (CDI), diethyl cyanophosphonate (DEPC), diisopropylcarbodiimide (DIPCI), benzotriazol-1-yloxy-trispyrrolidinophosphonium hexafluorophosphate (PyBOP), 1-hydroxybenzotriazole (HOBt), hydroxysuccinimide (HOSu), dimethylaminopyridine (DMAP), 1-hydroxy-7-azabenzotriazole (HOAt), hydroxyphthalimide (HOPht), pentafluorophenol (Pfp-OH), 2-(1H-benzotriazol-1-yl)-1,1,3,3-tetramethyluronium hexafluorophosphate (HBTU), O-(7-azabenzotriazol-1-yl)-1,1,3,3-tetramethyluronium hexafluorophosphonate (HATU), O-benzotriazol-1-yl-1,1,3,3-tetramethyluronium tetrafluoroborate (TBTU), and 3,4-dihydro-3-hydrodi-4-oxa-1,2,3-benzotriazine (Dhbt).

Examples of the solvent can include dimethyl sulfoxide (DMSO), N,N-dimethylformamide (DMF), and dichloromethane (DCM).

The amount of the activator used is 0.1 to 20 equivalents, preferably 0.5 to 10 equivalents, more preferably 0.8 to 5 equivalents, with respect to the amount of the carboxylic acid compound represented by the formula (2). The reaction can be performed in the solvent and may be performed at 0 to 50° C., preferably at room temperature, for approximately 10 to 30 hours, preferably for approximately 15 minutes to 24 hours. Moreover, reaction performed in a column for solid-phase synthesis is preferable, because it can be used directly in subsequent solid-phase synthesis.

The removal of the protecting group can be performed in the same way as above.

Step (B): Peptide Excision

Treatment with an acid is preferable for cleaving the peptide chain from the resin. Examples of the acid used can include mineral acids such as dilute hydrochloric acid and dilute sulfuric acid, and carboxylic acids such as formic acid and acetic acid. Examples of the dilute hydrochloric acid or dilute sulfuric acid include an aqueous solution of hydrochloric acid or sulfuric acid having a normality on the order of 0.01 to 2 N, preferably 0.05 to 1 N. Among these acids, acetic acid is preferable. The amount of the acid used is not particularly limited as long as it is 1 equivalent or more with respect to 1 equivalent of the peptide. For example, the amount may be approximately 1 to 10000 equivalents, preferably approximately 10 to 1000 equivalents.

This reaction is preferably performed in the presence of an alcohol. Examples of the alcohol include lower alcohols such as methanol, ethanol, and propanol, and halogenoalcohols such as trifluoroethanol (TFE) and trichloroethanol. Among these alcohols, methanol or trifluoroethanol is preferable. Trifluoroethanol is particularly preferable. The proportion of the alcohol used may be 0.1 to 2 volumes, preferably 0.5 to 1.5 volumes, more preferably 0.8 to 1.2 volumes of the alcohol with respect to 1 volume of the acid.

Moreover, an organic solvent such as DCM, DMF, or DMSO may also be used, if necessary, in this reaction.

The amount of the solvent used is not particularly limited and may be approximately 0.1 to 100 volumes with respect to 1 volume of the acid.

The reaction may be performed at 0 to 50° C., preferably at room temperature, for approximately 1 to 30 hours.

In this way, a peptide having a carboxyl group at the C-terminus can be obtained.

Step (C): Production of Peptide Thioester Compound

A thiol compound can be allowed to act on the obtained peptide (raw material peptide) in the presence of a condensing agent in a solvent to thereby produce a peptide having thioester at the C-terminus. Examples of the thiol compound can include benzyl mercaptans or lower alkanethiols (e.g., methanethiol and ethanethiol) which may have, at arbitrary position(s) in the phenyl ring, any number of substituents such as halogen atoms (e.g., fluorine, chlorine, bromine, and iodine), lower alkyl groups having 1 to 4 carbon atoms (e.g., methyl and ethyl groups), alkoxy groups having 1 to 4 carbon atoms (e.g., methoxy and ethoxy groups), and a nitro group. Among these thiol compounds, benzyl mercaptan is particularly preferable.

The amount of the thiol compound used may be 1 to 100 equivalents, preferably 10 to 80 equivalents, more preferably 20 to 50 equivalents, with respect to 1 equivalent of the raw material peptide. Particularly, an excessive amount of the thiol compound, preferably approximately 30 equivalents or more of the thiol compound, is preferably used for reducing the C-terminal racemization of the peptide.

Examples of the solvent used include THF, DCM, DMSO, and DMF. Among them, DMF is preferable.

Examples of the condensing agent can include HOBt/DIPCI and PyBOP/DIPEA. PyBOP/DIPEA is preferable.

The ratio of HOBt/DIPCI used may be 0.1 to 10 equivalents, preferably 0.5 to 5 equivalents, more preferably 0.8 to 1.2 equivalents of DIPCI with respect to 1 equivalent of HOBt.

The ratio of PyBOP/DIPEA used may be 0.1 to 10 equivalents, preferably 0.5 to 5 equivalents, more preferably 0.8 to 1.2 equivalents of DIPEA with respect to 1 equivalent of PyBOP.

The proportion of HOBt used may be 1 to 20 equivalents, preferably 3 to 15 equivalents, more preferably 8 to 12 equivalents, with respect to 1 equivalent of the raw material peptide.

The proportion of PyBOP used may be 1 to 10 equivalents, preferably 2 to 8 equivalents, more preferably 3 to 6 equivalents, with respect to 1 equivalent of the raw material peptide.

In this reaction, a dehydrating agent such as a molecular sieve is preferably used. Peptide racemization occurs when the C-terminal carboxylic acid of the raw material peptide is activated. Therefore, the reaction is preferably performed by mixing the raw material peptide with the thiol compound and then adding the condensing agent thereto. The reaction may be performed at a temperature of −100 to 0° C., preferably −80 to −10° C., for approximately 30 minutes to 2 hours.

The ratio of racemization of the peptide obtained in the present invention is reduced and is usually 6% or less, preferably 4% or less, more preferably 2% or less, particularly preferably 0 to 1%.

BEST MODE FOR CARRYING OUT THE INVENTION

Hereinafter, the present invention will be described with reference to Examples. However, the present invention is not intended to be limited to these Examples by any means.

Fmoc-protected amino acids used are known in the art and can be commercially available or prepared easily by introducing an Fmoc group into amino acids.

Moreover, Fmoc-Ala, Fmoc-Asn, Fmoc-Gly, Fmoc-Leu, Fmoc-Met, Fmoc-Phe, Fmoc-Pro, and Fmoc-Val mean that the amino group of each amino acid is protected with an Fmoc group. Boc-Cys(Acm) means that the cysteine amino group and thiol are protected with Boc and acetamidomethyl groups, respectively. Fmoc-Arg(Pbf) means $N^G$-(2,2,4,6,7-pentamethyldihydrobenzofuran-5-sulfonyl)arginine having an arginine α-amino group protected with an Fmoc group. Fmoc-Asp(OtBu) and Fmoc-Glu(OtBu) mean that the amino group of each amino acid and the aspartic acid β- or glutamic acid γ-carboxyl group are protected with Fmoc and tert-butyl groups, respectively. Fmoc-Cys(trt) means that the cysteine amino group and thiol are protected with Fmoc and trityl groups, respectively. Fmoc-Lys(Boc) means that the lysine α- and ε-amino groups are protected with Fmoc and Boc groups, respectively. Fmoc-Ser(tBu), Fmoc-Tyr(tBu), and Fmoc-Thr (tBu) mean that the amino and hydroxyl groups of each amino acid are protected with Fmoc and trityl groups, respectively. Boc-Leu and (Boc)Leu mean that the leucine amino group is protected with a Boc group. (Boc)Lys(Boc) means that the lysine α- and ε-amino groups are protected with a Boc group. Lys(Boc) means that the lysine ε-amino group is protected with a Boc group. Boc-Cys(Thz) means N-t-Boc-1,3-thiazolidine-4-carboxylic acid. Thr(tBu), Tyr(tBu), and Ser(tBu) mean that the hydroxyl group of each amino acid is protected with a tert-butyl group. His(trt) means that the imidazole nitrogen is protected with a trityl group. Cys(trt) means that the cysteine thiol group is protected with a trityl group. Gln (trt) means that amide nitrogen of glutamine is protected with a trityl group. Asp(OtBu) and Glu(OtBu) mean that the aspartic acid β- or glutamic acid γ-carboxyl group is protected with a tert-butyl group. Cys(Thz) means 1,3-thiazolidine-4-carbonyl. Arg(Pbf) means $N^G$-(2,2,4,6,7-pentamethyldihydrobenzofuran-5-sulfonyl)arginine.

These protecting groups can be introduced according to a method previously known in the art. Alternatively, commercially available amino acids protected with these protecting groups can be used. Moreover, Ph represents a phenyl group, and Bn represents a benzyl group.

$^1$H-NMR was measured using Bruker AVANCE 400 (indicated in 400 MHz).

An ESI mass spectrometer used was Esquire 3000 plus manufactured by Bruker Daltonics, and a MALDI mass spectrometer used was Autoflex manufactured by Bruker Daltonics. Dihydroxybenzoic acid was used in matrix.

Example 1

An amino-PEGA resin (1 g, 50 μmol) was placed in a column for solid-phase synthesis. The resin was thoroughly washed with DCM and DMF and then fully swollen with DMF. 4-hydroxymethyl-3-methoxyphenoxybutyric acid (HMPB) (30.1 mg, 0.13 mmol), TBTU (40.1 mg, 0.13 mmol), and N-ethylmorpholine (15.8 μl, 0.13 mmol) dissolved in DMF (1 ml) were placed in the column, and the mixture was stirred at room temperature for 2 hours. The resin was thoroughly washed with DMF and DCM to obtain an HMPB-PEGA resin, which was in turn used as a solid phase for solid-phase synthesis.

Fmoc-Phe (96.8 mg, 0.25 mmol), MSNT (74 mg, 0.25 mmol), and N-methylimidazole (15 μl, 0.19 mmol) dissolved in DCM (1 ml) were placed in the column for solid-phase synthesis, and the mixture was stirred at room temperature for 2 hours. After stirring, the resin was washed with DCM and DMF. The Fmoc group was removed with 20% piperidine/DMF solution (1 ml) for 20 minutes. After washing with DMF, amino acids were sequentially condensed according to a method shown below to elongate a peptide chain.

An amino acid having an amino group protected with an Fmoc group was dissolved, together with HOBt (33.8 mg, 0.25 mmol) and DIPCI (38 μl, 0.25 mmol), in DMF (1 ml) and activated for 15 minutes, and the mixture was then placed in the column for solid-phase synthesis and stirred at room temperature for 1.5 hours. Then, the Fmoc group was removed with 20% piperidine/DMF solution (1 ml) for 20 minutes. This procedure was repeated to sequentially condense amino acids.

Fmoc-Tyr(tBu) (114.9 mg, 0.25 mmol), Fmoc-Asn (88.6 mg, 0.25 mmol), Fmoc-Ala (77.8 mg, 0.25 mmol), Fmoc-His (trt) (154.9 mg, 0.25 mmol), Fmoc-Ser(tBu) (95.9 mg, 0.25 mmol), Fmoc-Asp(OtBu) (102.9 mg, 0.25 mmol), Fmoc-Leu (88.4 mg, 0.25 mmol), Fmoc-Val (84.9 mg, 0.25 mmol) were used as the amino acids having an amino group protected with an Fmoc group to form a 19-residue peptide of Phe-Tyr(tBu)-Tyr(tBu)-Asn-Ala-His(trt)-Ser(tBu)-His(trt)-Asp(OtBu)-Leu-Asn-Tyr(tBu)-Leu-Phe-Phe-Ser(tBu)-Val-Ser(tBu)-Asn (SEQ ID NO: 1) on the solid-phase resin.

After washing with DCM and DMF, the resin corresponding to 2 μmol of the 19-residue peptide was transferred to an Eppendorf tube.

A dibenzyl form of glycosylated asparagine (10 mg, 3.6 μmol) represented by the following formula (5) and DEPBT (2 mg, 6 μmol) dissolved in DMF (0.12 ml) were placed in the Eppendorf tube.

(5)

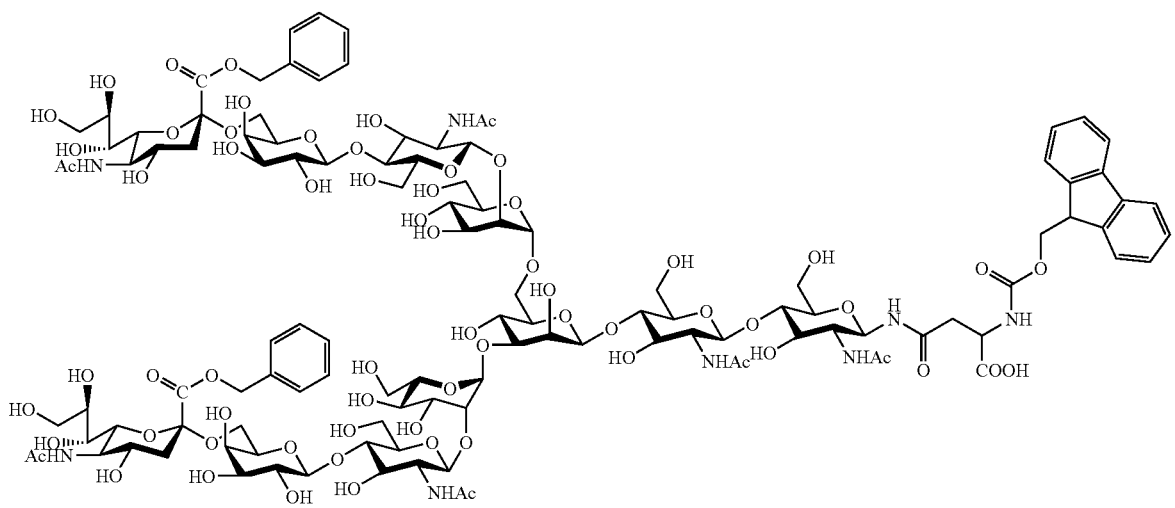

DIPEA (0.68 μl, 4 μmol) was added thereto, and the mixture was stirred at room temperature for 18 hours. After washing with DMF, the Fmoc group was removed with 20% piperidine to form a 20-residue peptide of Phe-Tyr(tBu)-Tyr(tBu)-Asn-Ala-His(trt)-Ser(tBu)-His(trt)-Asp(OtBu)-Leu-Asn-Tyr(tBu)-Leu-Phe-Phe-Ser(tBu)-Val-Ser(tBu)-Asn-Asn(Oligosaccharide chain) (SEQ ID NO: 2) represented by the formula (6) on the solid-phase resin.

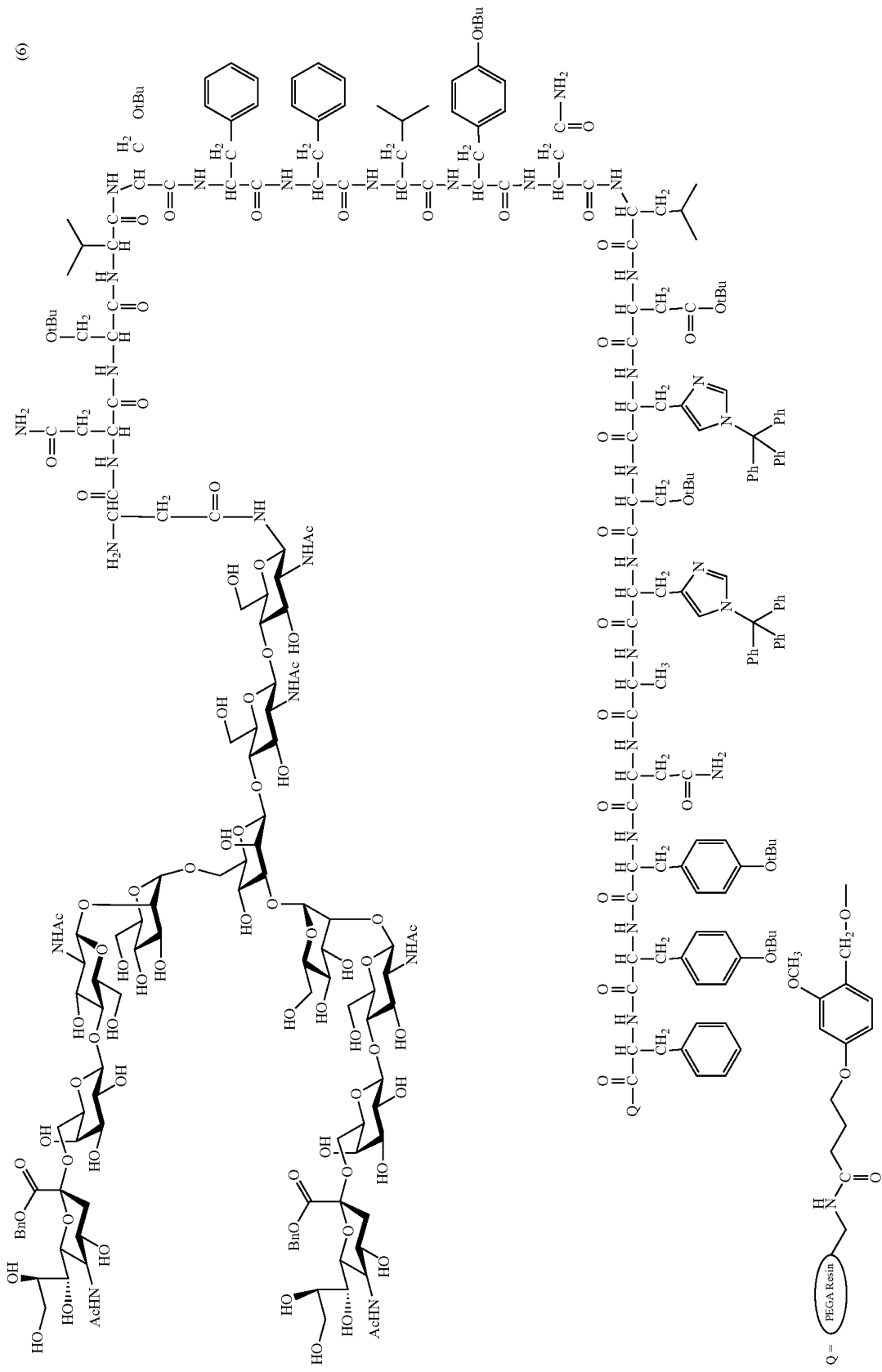

Example 2

An aliquot of the resin on which the 20-residue peptide obtained in Example 1 was formed was taken into a column for solid-phase synthesis. Acetic acid:DCM:methanol (=5:4:1) was added thereto such that the resin was fully immersed in the solution. The mixture was stirred at room temperature for 3 hours. The resin was removed by filtration, and the reaction solution was concentrated under reduced pressure. The obtained residue was purified by HPLC (Cadenza column C18 75×4.6 mm, developing solvent A: 0.1% aqueous TFA solution, B: 0.1% TFA acetonitrile:water=90:10, gradient A:B=60:40→0:100, 15 min, flow rate: 0.1 ml/min) to obtain a 20-residue peptide represented by the formula (7) (SEQ ID NO: 2).

The obtained peptide had a carboxyl group at the C-terminus, with the side chain protecting groups maintained.

ESI-MS: Calcd for $C_{279}H_{382}N_{34}O_{94}$:

$[M+3H]^{3+}$ 1906.3. found. 1905.8

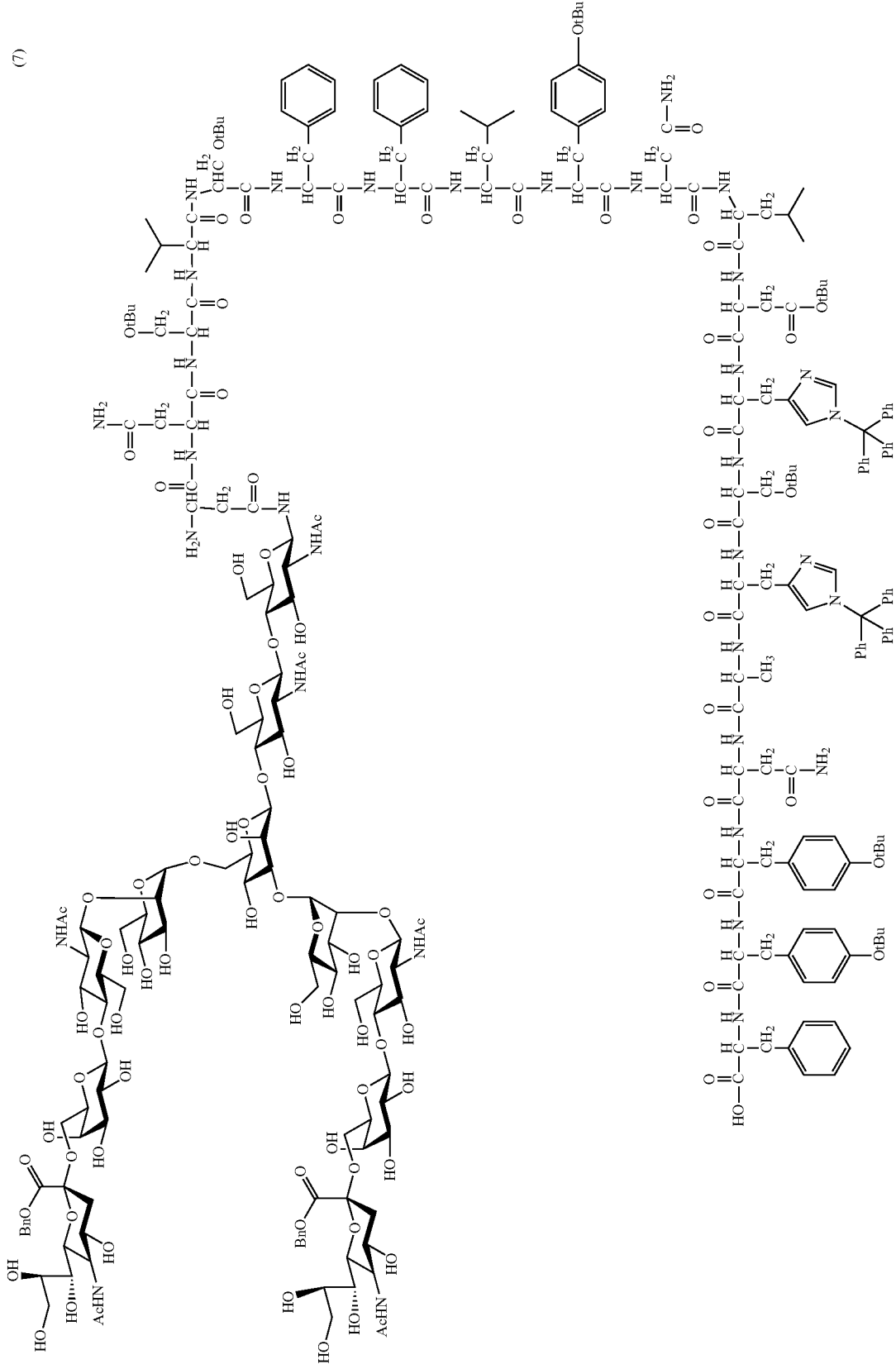

Example 3

The mixed solvent of acetic acid:DCM:methanol and the reaction time used in Example 2 were changed to acetic acid:TFE:DMC (=2:2:6) and 2 hours or to acetic acid:TFE (=1:1) and 27 hours, respectively, for reaction.

In both cases, the 20-residue peptide (7) (SEQ ID NO: 2) could be obtained.

However, the condition of acetic acid:TFE:DMC gave a yield approximately 5 times higher than that given under the condition of acetic acid:DCM:methanol. Furthermore, the condition of acetic acid:TFE gave a yield approximately 8 times higher than that given under the condition of acetic acid:DCM:methanol.

Example 4

An HMPB-PEGA resin (25 µmol) was obtained in the same way as in Example 1 and used as a solid phase for solid-phase synthesis. Amino acids were condensed thereon to form a peptide. The amino acid condensation was performed in the same way as in Example 1. Fmoc-Ala (38.9 mg, 0.13 mmol) was used as the first amino acid and condensed using MSNT (37 mg, 0.13 mmol), N-methylimidazole (7.5 µl, 94 µmol), and DCM (0.5 ml).

Then, amino acids having a protected amino group were sequentially condensed using HOBt (16.9 mg, 0.13 mmol), DIPCI (19.2 µl, 0.13 mmol), and DMF (0.5 ml). Fmoc-Gln (46.1 mg, 0.13 mmol), Fmoc-Thr(tBu) (49.7 mg, 0.13 mmol), Fmoc-Ile (44.2 mg, 0.13 mmol), Fmoc-Val (42.4 mg, 0.13 mmol), and Fmoc-Ser(tBu) (47.9 mg, 0.13 mmol) were sequentially used for condensation as the amino acids having a protected amino group.

After peptide elongation, the dibenzyl form of glycosylated asparagine (10 mg, 3.6 µmol) represented by the formula (5), DEPBT (2 mg, 6 µmol), DIPEA (0.68 µl, 4 µmol), and DMF (0.12 ml) were used for 2 µmol of the resin. Boc-Cys(Acm) (2.9 mg, 10 µmol) was then condensed using HOBt (1.36 mg, 10 µmol), DIPCI (1.54 µl, 10 µmol), and DMF (0.25 ml).

AcOH:TFE=1:1 (1 ml) was added to the resin, and the mixture was reacted at room temperature for 14 hours. The resin was removed by filtration, and the reaction solution was concentrated. The residue was purified by HPLC (Cadenza column C18 75×4.6 mm, developing solvent A: 0.1% aqueous TFA solution, B: 0.1% TFA/acetonitrile:water=90:10, gradient A:B=60:40→0:100, 15 min, flow rate: 0.1 ml/min) to obtain a 9-residue peptide having protected side chains, which is represented by the formula (8) (SEQ ID NO: 3).

ESI-MS: Calcd for $C_{155}H_{249}N_{18}O_{79}S$: $[M+2H]^{+2}$ 1830.3. found. 1831.0.

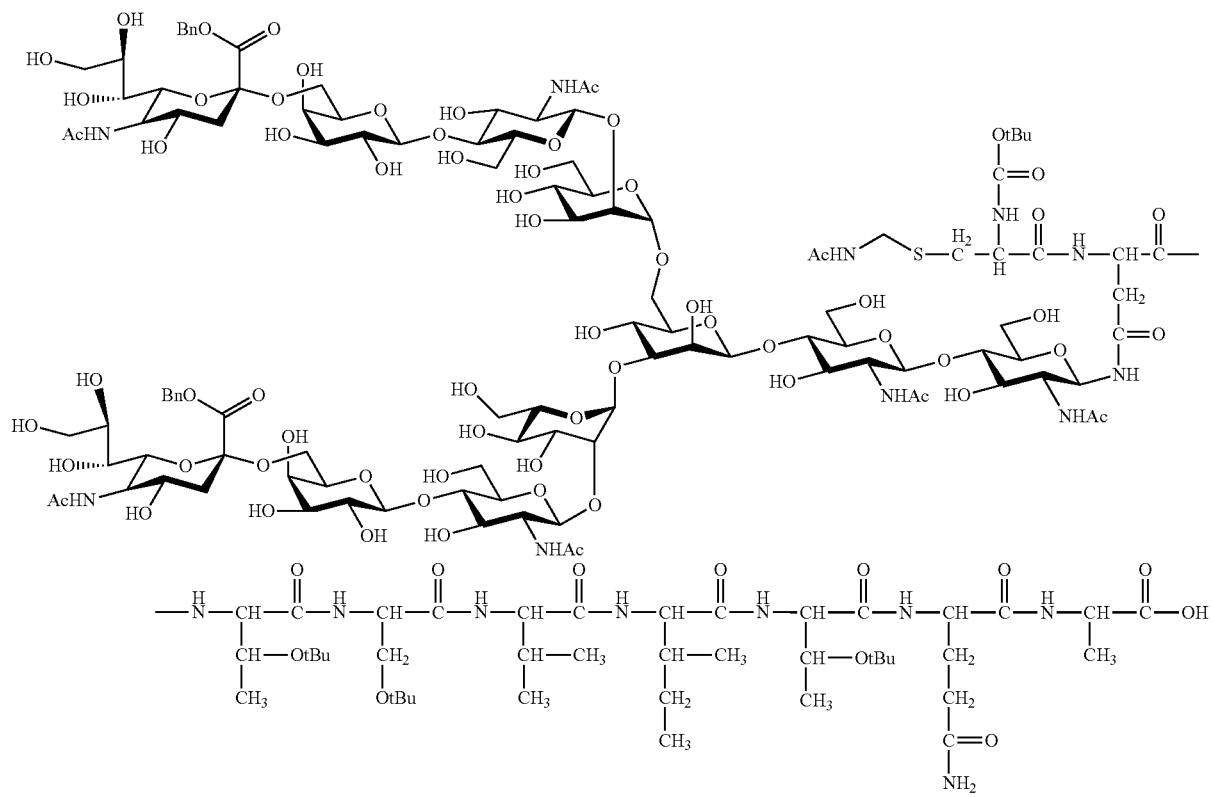

(8)

Example 5

The 9-residue peptide (8) (2 mg, 0.55 µmol) produced in Example 4, a molecular sieve (MS) 4 A (10 mg), and benzyl mercaptan (2 µl, 16.4 µmol) were stirred at −20° C. for 1 hour under argon flow in a DMF solvent (85 µl). PyBOP (1.4 mg, 2.7 µmol) and DIPEA (0.46 µl, 2.7 µmol) were then added thereto, and the mixture was stirred for 4 hours. Diethyl ether (5 ml) was then added to the reaction solution to precipitate a compound. After filtration, the pellet was collected using 50% aqueous acetonitrile solution, and this pellet was freeze-dried. To the obtained freeze-dried product, 95% aqueous TFA solution was added, and the mixture was stirred at room temperature for 2 hours. The resin was removed by filtration, and the reaction solution was concentrated. The concentrate was then dissolved in 50% aqueous acetonitrile solution and freeze-dried. The freeze-dried product was purified by HPLC (Cadenza column C18 75×4.6 mm, developing solvent A: 0.1% aqueous TFA solution, B: 0.1% TFA acetonitrile:water=90:10, gradient A:B=95:5→25:75, 15 min, flow rate: 0.1 ml/min) to produce a peptide having benzyl thioester at the C-terminus (NH$_2$-Cys(Acm)-Asn(disialooligo)-Thr-Ser-Val-Ile-Thr-Gln-Ala-COSBn), which is represented by the formula (9) (SEQ ID NO: 4).

(10 mg), and benzyl mercaptan (3.7 mg, 30 µmol) were stirred at −20° C. for 1 hour under argon flow in a DMF solvent (0.14 ml). PyBOP (2.6 mg, 5 µmol) and DIPEA (0.85 µl, 5 µmol) were then added thereto, and the mixture was stirred for 17 hours. Diethyl ether (5 ml) was then added to the reaction solution to precipitate a compound. After filtration, the pellet was collected using 50% aqueous acetonitrile solution. This pellet was purified by HPLC (Cadenza column C18 75×4.6 mm, developing solvent A: 0.1% aqueous TFA solution, B: 0.1% TFA acetonitrile:water=90:10, gradient A:B=70:30→40:60, 15 min, flow rate: 0.1 ml/min) to obtain a peptide having benzyl thioester at the C-terminus (AcNH-His-Ala-Ala-Phe-COSBn) (SEQ ID NO: 6).

(9)

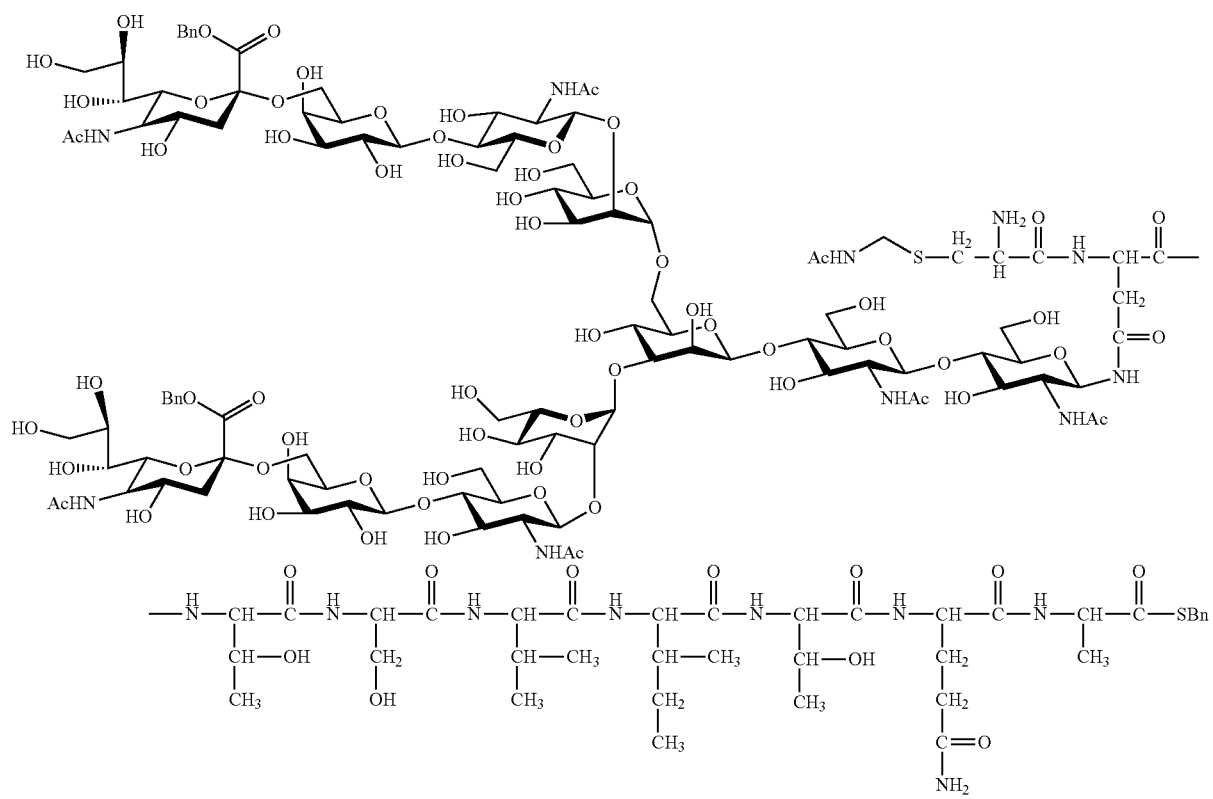

$^1$H-NMR (400 MHz, 295 K in D$_2$O, HOD=δ4.81)

7.53-7.33 (m, 15H, Ph×3), 5.37 (d, 2H, J=11.7 Hz, PhCH$_2$), 5.29 (d, 2H, J=11.6 Hz, PhCH$_2$), 5.11 (s, 1H, Man4-H-1), 5.02 (d, 1H, GlcNAc1-H-1), 4.92 (s, 1H, Man4'-H-1), 4.65-4.52 (m, 3H, GlcNAc2,5,5'-H-1), 2.91-2.78 (m, 4H, Asn-βCH$_2$, Cys-.βCH$_2$), 2.67 (dd, 2H, NeuAc7,7'-H$_{3eq}$), 2.39-2.31 (m, 2H, Gln-γCH$_2$), 1.83 (dd, 2H, J=13.1, 13.1 Hz, NeuAc7,7'-H-3$_{ax}$), 1.38 (d, 3H, Ala-βCH$_3$), 1.20 (d, 3H, J=6.51 Hz, Thr-γCH$_3$), 1.17 (d, 3H, J=6.40 Hz, Thr-γCH$_3$), 0.95-0.80 (m, 12H, Val-γCH$_3$, Ile-.γCH$_3$, .CH$_3$)

ESI-MS: Calcd for C$_{145}$H$_{223}$N$_{18}$O$_{76}$S: [M+2H]$^{2+}$ 1749.8. found. 1749.2

Example 6

A peptide having a carboxyl group at the C-terminus (AcNH-His-Ala-Ala-Phe-COOH) (SEQ ID NO: 5) was produced according to a method previously known in the art and used as a raw material. The peptide (0.5 mg, 1 µmol), MS 4 A The ratio of racemization was 2% or less.
ESI-MS: Calcd for C$_{30}$H$_{36}$N$_6$O$_5$S: [M+H]$^+$ 592.3. found. 592.2

Example 7

A benzyl thioester form of a peptide (AcNH-His-Ala-Ala-Phe-COSBn) (SEQ ID NO: 6) was obtained by the same procedures as in Example 6 except that the reaction temperature was changed to 0° C. The obtained compound had the same mass spectrum as that obtained in Example 6. The ratio of racemization was 6%.

Example 8

The peptide of AcNH-His-Ala-Ala-Phe-COOH (0.5 mg, 1 µmol) (SEQ ID NO: 5), MS 4 A (10 mg), and HOBt (0.7 mg, 5 µmol or 1.4 mg, 10 µmol) were stirred at 0° C. for 1 hour under argon flow in a DMF solvent (0.14 ml). DIPCI (0.8 µl, 5 µmol or 1.6 µl, 10 µmol) and benzyl mercaptan (3.7 mg, 30 µmol) were then added thereto. Subsequent procedures were performed in the same way as in Example 6 to obtain a benzyl thioester form of a peptide (AcNH-His-Ala-Ala-Phe-COSBn) (SEQ ID NO: 6). Its yield was 75% for the use of 5 equivalents of HOBt and 98% for the use of 10 equivalents of HOBt. The obtained compound had the same mass spectrum as that obtained in Example 6. The ratio of racemization was 5% in either case.

Example 9

A peptide having a carboxyl group at the C-terminus (AcNH-Cys-Cys-Glu-His-COOH) (SEQ ID NO: 7) was produced according to a method previously known in the art and used as a raw material. The peptide (0.5 mg, 1 µmol), MS 4 A (10 mg), and HOBt (1.4 mg, 10 µmol) were stirred at −20° C. for 1 hour under argon flow in a DMF solvent (0.14 ml). DIPCI (1.6 µl, 10 µmol) and benzyl mercaptan (3.7 mg, 30 µmol) were then added thereto for reaction. Subsequent procedures were performed in the same way as in Example 6 to obtain a benzyl thioester form of a peptide (AcNH-Cys-Cys-Glu-His-COSBn) (SEQ ID NO: 8).

The ratio of racemization was 2% or less.

Example 10

A trityl chloride resin (150 µmol) was used as a solid phase for solid-phase synthesis. Amino acids were sequentially condensed thereon to form a peptide. The amino acid condensation was performed in the same way as in Example 1.

Fmoc-Leu (159.0 mg, 0.45 mmol) was used as the first amino acid and condensed using DCM (0.9 ml) and DIEA (204.1 µl, 1.2 mmol).

Then, amino acids having a protected amino group were sequentially condensed using HOBt (101.3 mg, 0.75 mmol), DIPCI (115.4 µl, 0.75 mmol), and DMF (3 ml).

Fmoc-Pro (253.1 mg, 0.75 mmol), Fmoc-Arg(Pbf) (486.6 mg, 0.75 mmol), Fmoc-Tyr(tBu) (334.7 mg, 0.75 mmol), Fmoc-Glu(OtBu) (319.2 mg, 0.75 mmol), Fmoc-Met (278.6 mg, 0.75 mmol), Fmoc-Thr(tBu) (298.1 mg, 0.75 mmol), Fmoc-Cys(trt) (439.3 mg, 0.75 mmol), Fmoc-Ala (233.5 mg, 0.75 mmol), Fmoc-Pro (253.1 mg, 0.75 mmol), Fmoc-Lys (Boc) (351.4 mg, 0.75 mmol), Fmoc-Pro (253.1 mg, 0.75 mmol), Fmoc-Tyr(tBu) (334.7 mg, 0.75 mmol), Fmoc-Glu (OtBu) (319.2 mg, 0.75 mmol), Fmoc-Ser(tBu) (287.6 mg, 0.75 mmol), Fmoc-Cys(trt) (439.3 mg, 0.75 mmol), Fmoc-Asp(OtBu) (308.6 mg, 0.75 mmol), Fmoc-Val (254.6 mg, 0.75 mmol), Fmoc-Ser(tBu) (287.6 mg, 0.75 mmol), Fmoc-Val (254.6 mg, 0.75 mmol), Fmoc-Ala (233.5 mg, 0.75 mmol), Fmoc-Ala (233.5 mg, 0.75 mmol), Boc-Leu (187 mg, 0.75 mmol) were sequentially used for condensation as the amino acids having a protected amino group.

AcOH:DCM:MeOH=5:4:1 (1 ml) was added to the resin, and the mixture was reacted at room temperature for 3 hours. Hexane was added to the reaction solution. The resin was then removed by filtration. The resin was washed with MeOH, and the solution thereof was concentrated. The concentrated residue was further concentrated by the addition of benzene to obtain a 23-residue peptide having protected side chains ((Boc)Leu-Ala-Ala-Val-Ser(tBu)-Val-Asp(OtBu)-Cys(trt)-Ser(tBu)-Glu(OtBu)-Tyr(tBu)-Pro-Lys(Boc)-Pro-Ala-Cys (trt)-Thr(tBu)-Met-Glu(OtBu)-Tyr(tBu)-Arg(Pbf)-Pro-Leu-COOH) (10) (SEQ ID NO: 9).

The obtained 23-residue peptide (10) (39 mg, 10 µmol), MS 4 A, and benzyl mercaptan (35.5 µl, 300 µmol) were stirred at −20° C. for 1 hour under argon flow in a DMF solvent (1350 µl). PyBOP (26 mg, 50 µmol) and DIPEA (8.5 µl, 50 µmol) were then added thereto, and the mixture was stirred for 2 hours. Diethyl ether was then added to the reaction solution to precipitate a compound. After filtration, the pellet was collected using DMF. This pellet was concentrated. 95% aqueous TFA solution was added to the residue, and the mixture was stirred at room temperature for 2 hours and then freeze-dried.

The freeze-dried product was purified by HPLC (Cadenza column C18 75×4.6 mm, developing solvent A: 0.1% aqueous TFA solution, B: 0.1% TFA acetonitrile:water=90:10, gradient A:B=80:20→40:60, 15 min, flow rate: 1.0 ml/min) to produce a peptide having benzyl thioester at the C-terminus (Leu-Ala-Ala-Val-Ser-Val-Asp-Cys-Ser-Glu-Tyr-Pro-Lys-Pro-Ala-Cys-Thr-Met-Glu-Tyr-Arg-Pro-Leu-COSBn), which is represented by the formula (11) (SEQ ID NO: 10).

Yield: 20 mg

Ratio of racemization: 2% or less

ESI-MS: Calcd for $C_{118}H_{181}N_{27}O_{34}S_4$: $[M+2H]^{+2}$ 1325.1. found. 1325.3.

(11)

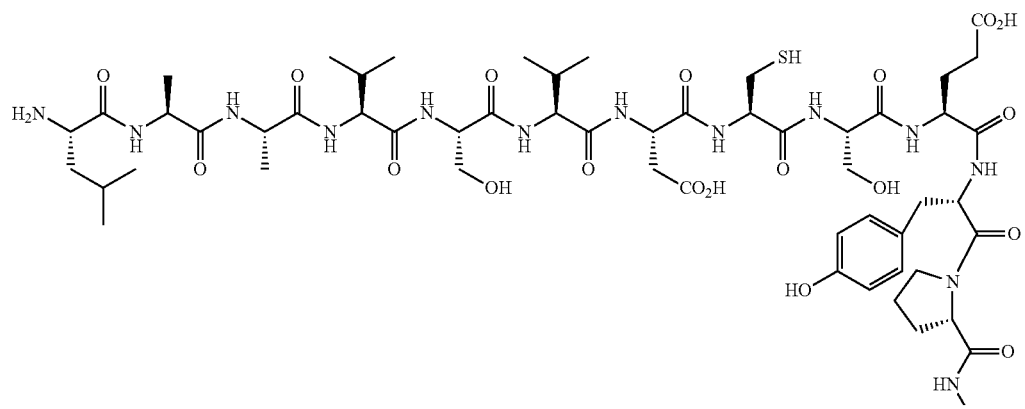

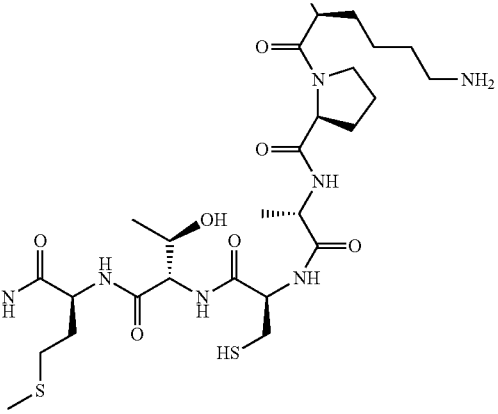

Example 11

Cys(Thz) (46.7 mg, 0.2 mmol) was condensed to a 26-residue peptide bonded to a trityl resin (40 μmol) as a solid phase (Glu(OtBu)-Tyr(tBu)-Ala-Ser(tBu)-Pro-Gly-Lys(Boc)-Ala-Thr(tBu)-Glu(OtBu)-Val-Arg(Pbf)-Val-Thr(tBu)-Val-Leu-Arg(Pbf)-Gln(trt)-Ala-Asp(OtBu)-Ser(tBu)-Gln(trt)-Val-Thr(tBu)-Glu(OtBu)-Gly-CO-(Trityl resin)) (SEQ ID NO: 11) (300 mg, product from Novabiochem) using HOBt (27.0 mg, 0.2 mmol), DIPCI (30.8 μl, 0.2 mmol), and DMF (1 ml).

1% TFA/DCM solution (1.0 ml) was added to the resin, and the mixture was reacted at room temperature for 2 minutes. The resin was removed by filtration, and the reaction solution was neutralized with pyridine. This reaction was repeated 5 times. The reaction solution was concentrated, and water was then added thereto to precipitate a peptide having protected side chains. The pellet was collected using a DMF solution and concentrated to obtain a 27-residue peptide having protected side chains (Cys(Thz)-Glu(OtBu)-Tyr(tBu)-Ala-Ser(tBu)-Pro-Gly-Lys(Boc)-Ala-Thr(tBu)-Glu(OtBu)-Val-Arg(Pbf)-Val-Thr(tBu)-Val-Leu-Arg(Pbf)-Gln(trt)-Ala-Asp(OtBu)-Ser(tBu)-Gln(trt)-Val-Thr(tBu)-Glu(OtBu)-Gly-COOH) (12) (SEQ ID NO: 12).

The obtained 27-residue peptide (12) (10 μmol), MS 4 A (20 mg), and thiophenol (30.6 μl, 300 μmol) were stirred at −20° C. for 1 hour under argon flow in a DMF solvent (1.36 μl). PyBOP (8.6 mg, 50 μmol) and DIPEA (26.0 μl, 50 μmol) were then added thereto, and the mixture was stirred for 4 hours. Diethyl ether was then added to the reaction solution to precipitate a compound. After filtration, the pellet was collected using DMF. This pellet was concentrated. 95% aqueous TFA solution was added to the concentrate, and the mixture was stirred at room temperature for 2 hours. The resin was removed by filtration, and the reaction solution was concentrated. The concentrate was then dissolved in 50% aqueous acetonitrile solution and freeze-dried. The freeze-dried product was purified by HPLC (Cadenza column C18 75×4.6 mm, developing solvent A: 0.1% aqueous TFA solution, B: 0.1% TFA acetonitrile:water=90:10, gradient A:B=95:5→25:75, 15 min, flow rate: 0.1 ml/min) to produce a peptide having phenyl thioester at the C-terminus (Cys(Thz)-Glu-Tyr-Ala-Ser-Pro-Gly-Lys-Ala-Thr-Glu-Val-Arg-Val-Thr-Val-Leu-Arg-Gln-Ala-Asp-Ser-Gln-Val-Thr-Glu-Gly-COSPh), which is represented by the formula (13) (SEQ ID NO: 13).

Yield: 5 mg
Ratio of racemization: 1% or less
ESI-MS: Calcd for $C_{128}H_{204}N_{36}O_{43}S_2$: $[M+2H]^{+2}$ 1499.7. found. 1499.8.

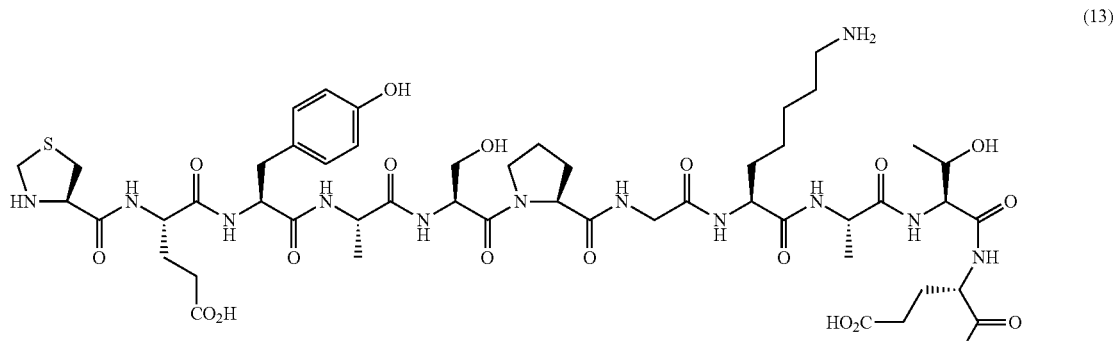

(13)

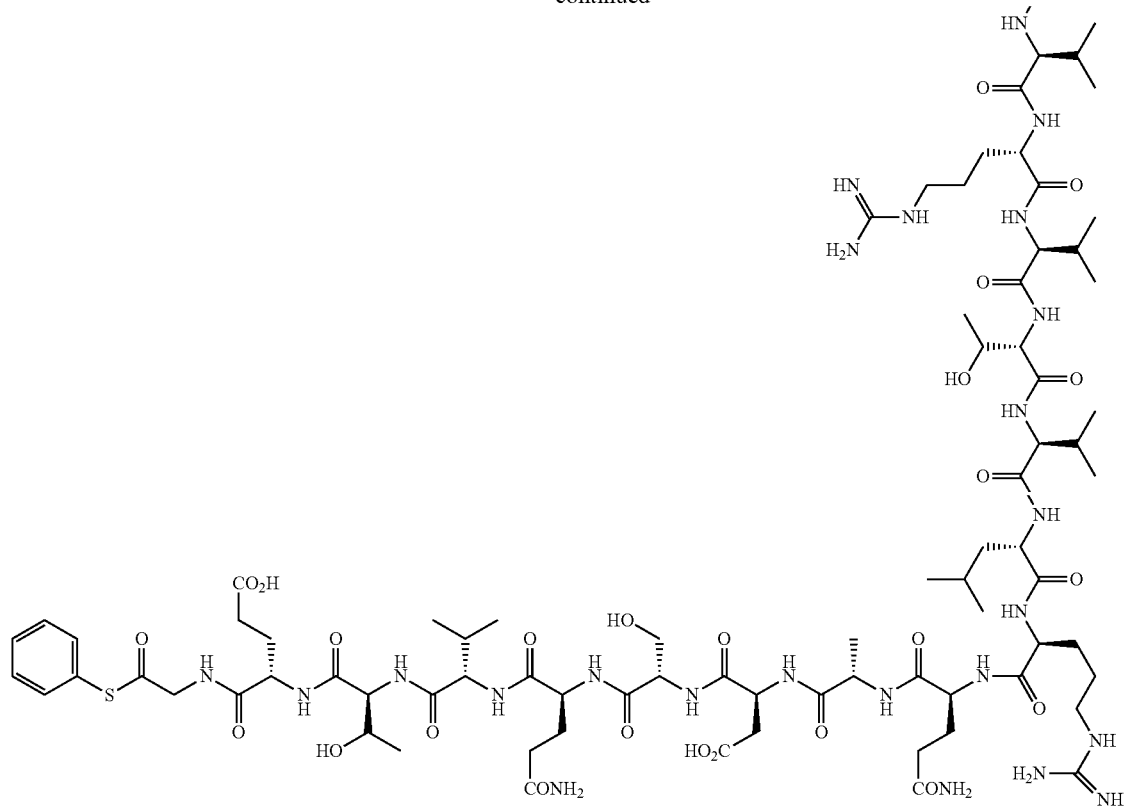

Example 12

Cys(Thz) (46.7 mg, 0.2 mmol) was condensed to a 17-residue peptide bonded to a trityl resin (40 μmol) as a solid phase (Ala-Ala-Thr(tBu)-Tyr(tBu)-Met-Met-Gly-Asn-Glu(OtBu)-Leu-Thr(tBu)-Phe-Leu-Asp(OtBu)-Asp(OtBu)-Ser(tBu)-Gly-CO-(Trityl resin)) (SEQ ID NO: 14) (500 mg, product from Novabiochem) using HOBt (27.0 mg, 0.2 mmol), DIPCI (30.8 μl, 0.2 mmol), and DMF (1 ml).

1% TFA/DCM solution was added to the resin, and the mixture was reacted at room temperature for 2 minutes. The resin was removed by filtration, and the reaction solution was neutralized with pyridine. This reaction was repeated 5 times. The reaction solution was concentrated, and water was then added thereto to precipitate a peptide having protected side chains. The pellet was collected using a DMF solution and concentrated to obtain a 18-residue peptide having protected side chains (Cys(Thz)-Ala-Ala-Thr(tBu)-Tyr(tBu)-Met-Met-Gly-Asn-Glu(OtBu)-Leu-Thr(tBu)-Phe-Leu-Asp(OtBu)-Asp(OtBu)-Ser(tBu)-Gly-COOH) (14) (SEQ ID NO: 15).

The obtained 18-residue peptide (14) (10 μmol), MS 4 A (20 mg), and benzyl mercaptan (36.0 μl, 300 μmol) were stirred at −20° C. for 1 hour under argon flow in a DMF solvent (1.36 μl). PyBOP (8.6 mg, 50 μmol) and DIPEA (26.0 μl, 50 μmol) were then added thereto, and the mixture was stirred for 4 hours. Diethyl ether was then added to the reaction solution to precipitate a compound. After filtration, the pellet was collected using DMF. This pellet was concentrated. 95% aqueous TFA solution (containing ethanedithiol (EDT)) was added to the concentrate, and the mixture was stirred at room temperature for 2 hours. The resin was removed by filtration, and the reaction solution was concentrated. The concentrate was then dissolved in 50% aqueous acetonitrile solution and freeze-dried. The freeze-dried product was purified by HPLC (Cadenza column C18 75×4.6 mm, developing solvent A: 0.1% aqueous TFA solution, B: 0.1% TFA/acetonitrile:water=90:10, gradient A:B=95:5→25:75, 15 min, flow rate: 0.1 ml/min) to produce a peptide having benzyl thioester at the C-terminus (Cys(Thz)-Ala-Ala-Thr-Tyr-Met-Met-Gly-Asn-Glu-Leu-Thr-Phe-Leu-Asp-Asp-Ser-Gly-COSBn), which is represented by the formula (15) (SEQ ID NO: 16).

Yield: 4 mg

Ratio of racemization: 1% or less

ESI-MS: Calcd for $C_{89}H_{129}N_{19}O_{29}S_4$: $[M+2H]^{+2}$ 2056.8. found. 2057.2.

(15)

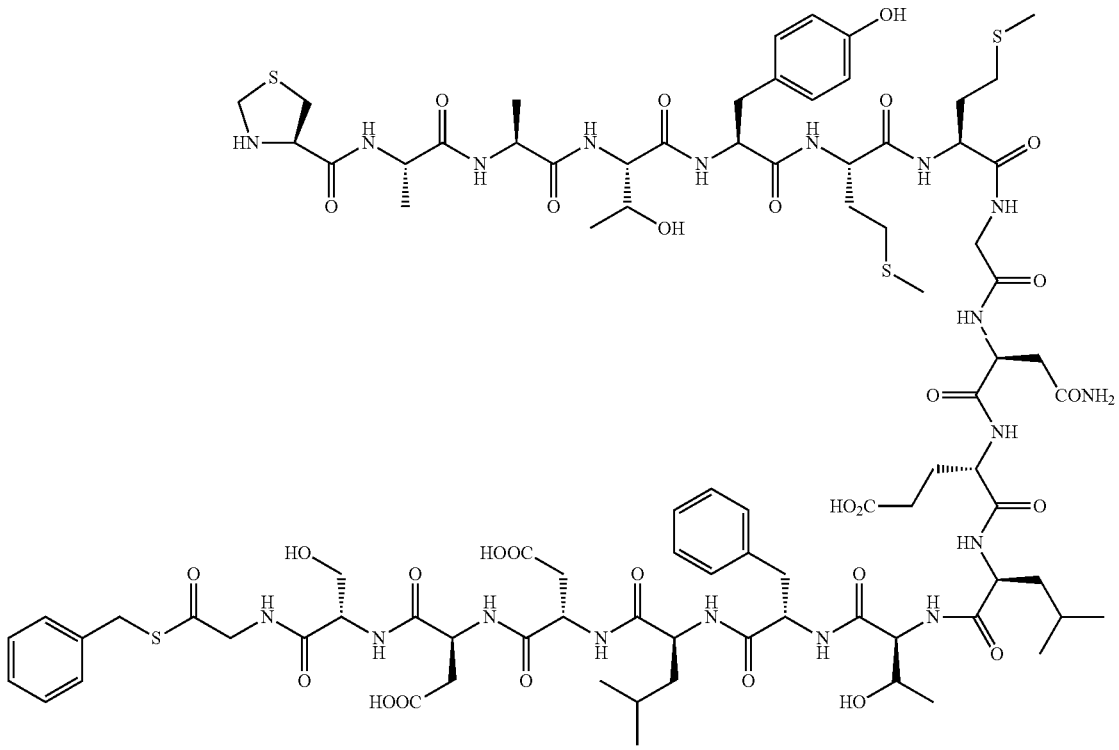

Example 13

1% TFA/DCM solution was added to a 22-residue peptide bonded to a trityl resin (20 μmol) as a solid phase ((Boc)Lys(Boc)-Ala-Met-His(trt)-Val-Ala-Gln(trt)-Pro-Ala-Val-Val-Leu-Ala-Ser(tBu)-Ser(tBu)-Arg(Pbf)-Gly-Ile-Ala-Ser(tBu)-Phe-Gly-CO-(Trityl resin)) (SEQ ID NO: 17) (250 mg, product from Novabiochem), and the mixture was reacted at room temperature for 2 minutes. The resin was removed by filtration, and the reaction solution was neutralized with pyridine. This reaction was repeated 5 times. The reaction solution was concentrated, and water was then added thereto to precipitate a peptide having protected side chains. The pellet was collected using a DMF solution and concentrated to obtain a 22-residue peptide having protected side chains ((Boc)Lys(Boc)-Ala-Met-His(trt)-Val-Ala-Gln(trt)-Pro-Ala-Val-Val-Leu-Ala-Ser(tBu)-Ser(tBu)-Arg(Pbf)-Gly-Ile-Ala-Ser(tBu)-Phe-Gly-COOH) (16) (SEQ ID NO: 17).

ESI-MS: Calcd for $C_{170}H_{245}N_{29}O_{34}S_2$: $[M+2H]^{+2}$ 1652.0. found. 1651.6

The obtained 22-residue peptide (16) (7.5 mg, 2.2 μmol), MS 4 A (20.0 mg), and thiophenol (6.7 μl, 11.0 μmol) were stirred at −20° C. for 1 hour under argon flow in a DMF solvent (300 μl). PyBOP (5.7 mg, 66.0 μmol) and DIPEA (1.7 μl, 11.0 μmol) were then added thereto, and the mixture was stirred for 4 hours. Diethyl ether was then added to the reaction solution to precipitate a compound. After filtration, the pellet was collected using DMF. This pellet was concentrated. 95% aqueous TFA solution was added to the concentrate, and the mixture was stirred at room temperature for 2 hours. The resin was removed by filtration, and the reaction solution was concentrated. The concentrate was then dissolved in 50% aqueous acetonitrile solution and freeze-dried. The freeze-dried product was purified by HPLC (Cadenza column C18 75×4.6 mm, developing solvent A: 0.1% aqueous TFA solution, B: 0.1% TFA/acetonitrile:water=90:10, gradient A:B=95:5→25:75, 15 min, flow rate: 0.1 ml/min) to produce a peptide having phenyl thioester at the C-terminus (Lys-Ala-Met-His-Val-Ala-Gln-Pro-Ala-Val-Val-Leu-Ala-Ser-Ser-Arg-Gly-Ile-Ala-Ser-Phe-Gly-COSPh), which is represented by the formula (17) (SEQ ID NO: 18).

Yield: 2 mg
Ratio of racemization: 1% or less
ESI-MS: Calcd for $C_{103}H_{165}N_{29}O_{26}S_2$: $[M+2H]^{+2}$ 1145.9. found. 1145.7.

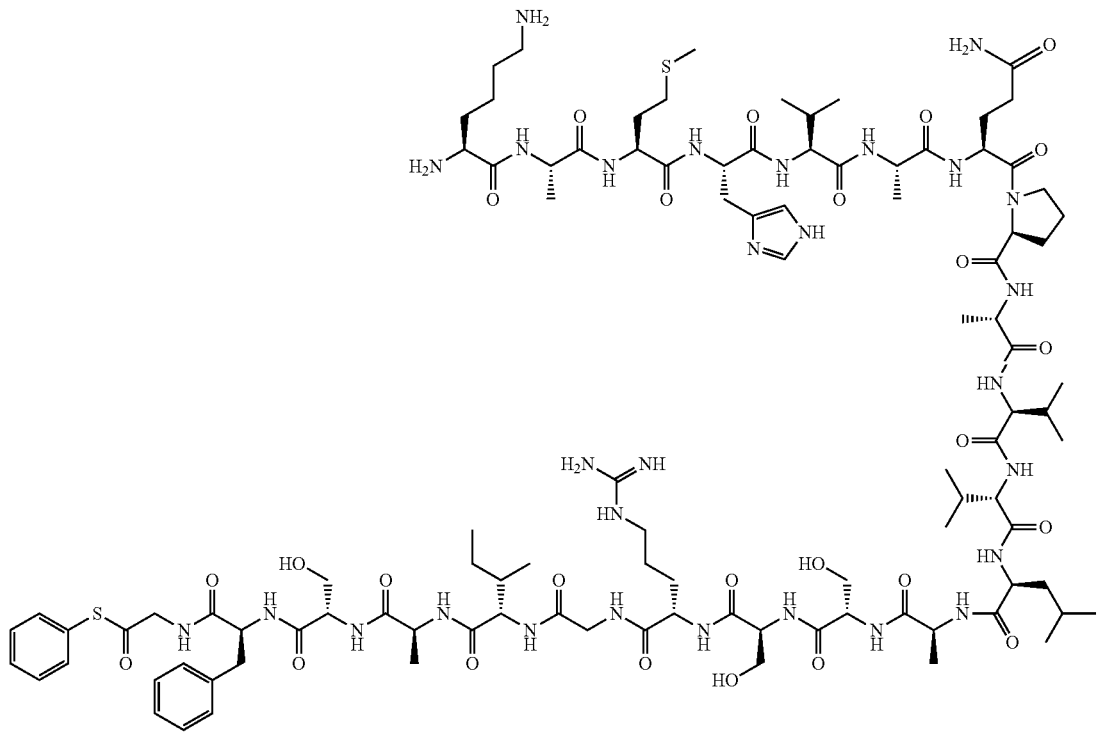

(17)

Example 14

An HMPB-PEGA resin (50 μmol) was obtained in the same way as in Example 1 and used as a solid phase for solid-phase synthesis. Amino acids were condensed thereon to form a peptide. The amino acid condensation was performed in the same way as in Example 1.

Fmoc-Phe (96.9 mg, 0.25 mmol) was used as the first amino acid and condensed using MSNT (74.0 mg, 0.25 mmol), N-methylimidazole (14.9 μl, 187.5 μmol), and DCM (1 ml).

Then, amino acids having a protected amino group were sequentially condensed using HOBt (33.7 mg, 0.25 mmol), DIPCI (38.5 μl, 0.25 mmol), and DMF (1 ml).

Fmoc-Asn (88.6 mg, 0.25 mmol), Fmoc-Cys(trt) (146.4 mg, 0.25 mmol), Fmoc-Lys(Boc) (117.1 mg, 0.25 mmol), Fmoc-Asn (88.6 mg, 0.25 mmol), Fmoc-Gly (74.3 mg, 0.25 mmol), Fmoc-Tyr(tBu) (114.9 mg, 0.25 mmol), Fmoc-Thr(tBu) (99.4 mg, 0.25 mmol), Fmoc-Lys(Boc) (117.1 mg, 0.25 mmol) were used as the amino acids having a protected amino group to form a 9-residue peptide of Phe-Asn-Cys(trt)-Lys(Boc)-Asn-Gly-Tyr(tBu)-Thr(tBu)-Lys(Boc) (SEQ ID NO: 19) on the solid-phase resin.

After washing with DCM and DMF, the resin corresponding to 3 μmol of the 9-residue peptide was transferred to an Eppendorf tube.

Glycosylated asparagine (12 mg, 6 μmol) represented by the following formula (18) and DEPBT (3 mg, 9 μmol) dissolved in DMF:DMSO=4:1 (201 μl) were placed in the Eppendorf tube.

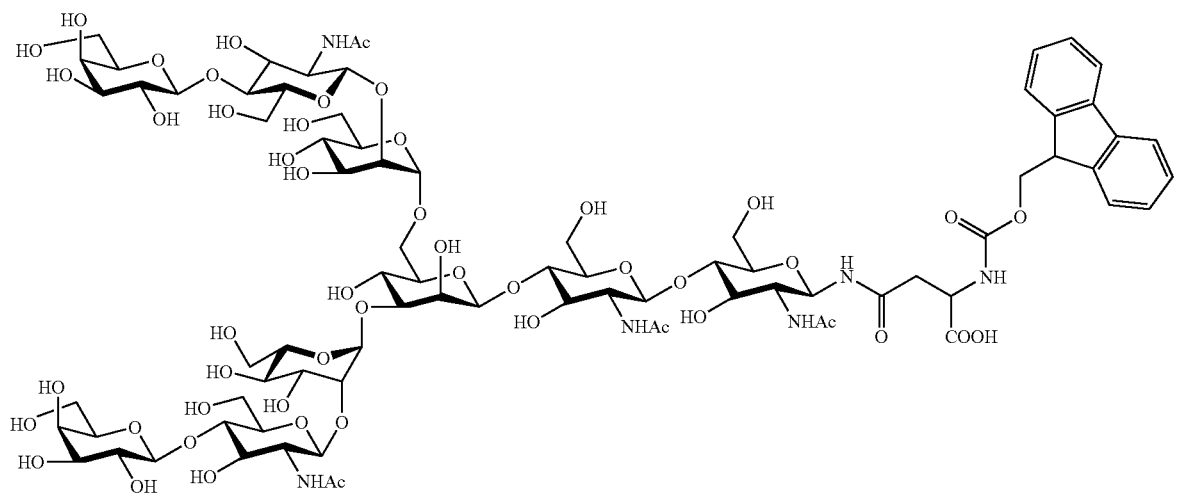

(18)

DIPEA (1.02 μl, 6 μmol) was added thereto, and the mixture was stirred at room temperature for 20 hours. After washing with DMF, the Fmoc group was removed with 20% piperidine to form a 10-residue peptide of Phe-Asn-Cys(trt)-Lys (Boc)-Asn-Gly-Tyr(tBu)-Thr(tBu)-Lys(Boc)-Asn (Oligosaccharide chain) (SEQ ID NO: 20) on the solid-phase resin.

Amino acids were further condensed to this 10-residue peptide in the same way as above using HOBt, DIPCI, and DMF.

Fmoc-Asp (1.7 mg, 0.015 mmol), Fmoc-Ser(tBu) (1.9 mg, 0.015 mmol), Fmoc-Gly (1.5 mg, 0.015 mmol), and Boc-Cys (Thz) (1.7 mg, 0.015 mmol) were sequentially used for condensation as the amino acids.

AcOH:TFE=1:1 (1 ml) was added to the resin, and the mixture was reacted at room temperature for 20 hours. The resin was removed by filtration, and the reaction solution was concentrated to obtain a 14-residue peptide having protected side chains (Cys(Thz)-Gly-Ser(tBu)-Asp-Asn(Oligosaccharide chain)-Lys(Boc)-Thr(tBu)-Tyr(tBu)-Gly-Asn-Lys (Boc)-Cys(trt)-Asn-Phe-COOH) (19) (SEQ ID NO: 21).

The obtained 14-residue peptide (19) (11.7 mg, 3 μmol), MS 4 A, and benzyl mercaptan (10.6 μl, 90 μmol) were stirred at −20° C. for 1 hour under argon flow in a DMF solvent (405 μl). PyBOP (7.8 mg, 15 μmol) and DIPEA (2.6 μl, 15 μmol) were then added thereto, and the mixture was stirred for 2 hours. Diethyl ether was then added to the reaction solution to deposit the compound of interest as a pellet. This pellet was separated from the solution by filtration, and the pellet remaining on the filter paper was dissolved in 50% aqueous acetonitrile solution and collected. The collected solution was concentrated. 95% aqueous TFA solution was added to the concentrate, and the mixture was stirred at room temperature for 2 hours and then freeze-dried. The freeze-dried product was purified by HPLC (Cadenza column C18 75×4.6 mm, developing solvent A: 0.01% aqueous TFA solution, B: 0.01% TFA/acetonitrile:water=90:10, gradient A:B=80:20→40:60, 15 min, flow rate: 1 ml/min) to produce a peptide having benzyl thioester at the C-terminus (Cys(Thz)-Gly-Ser-Asp-Asn(Oligosaccharide chain)-Lys-Thr-Tyr-Gly-Asn-Lys-Cys-Asn-Phe-COSBn), which is represented by the formula (20) (SEQ ID NO: 22).

Yield: 3 mg

The ratio of racemization was 2% or less.

ESI-MS: Calcd for $C_{133}H_{203}N_{23}O_{67}S_3$: $[M+2H]^{+2}$ 1646.1. found. 1646.4.

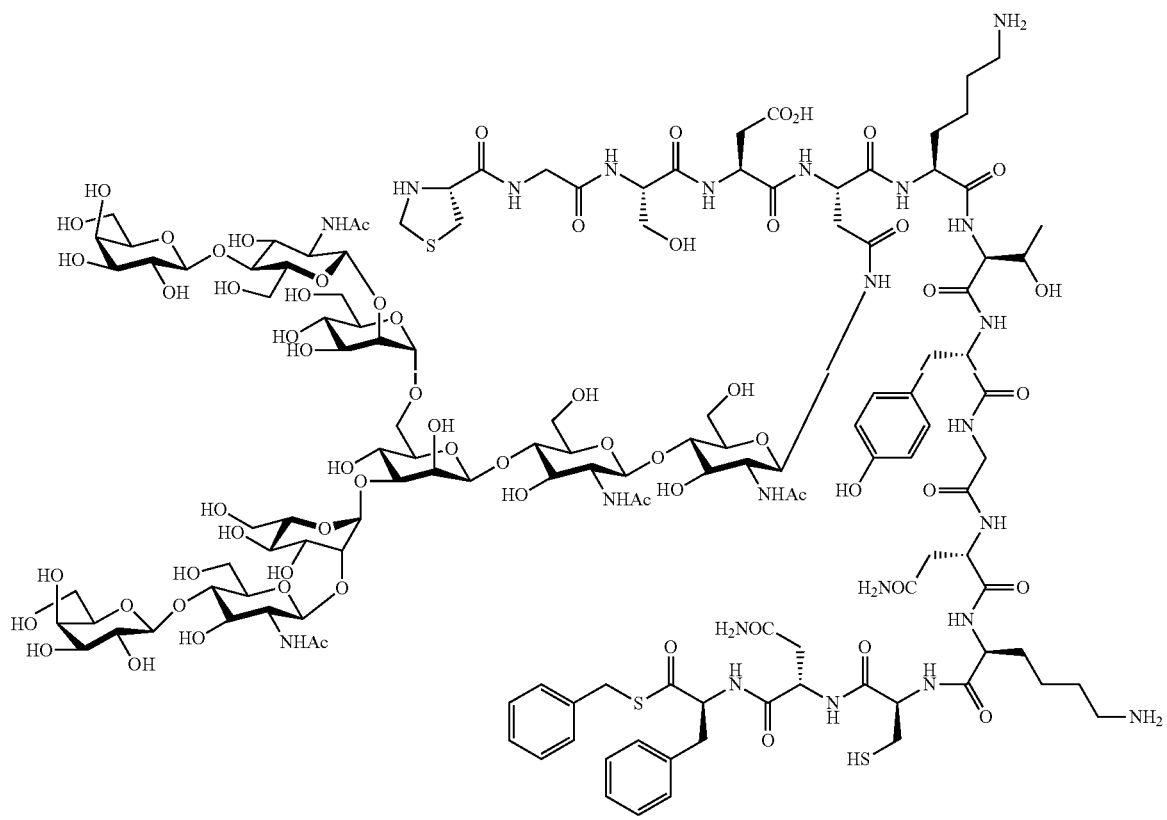

(20)

Comparative Example 1

A benzyl thioester form of a peptide (AcNH-His-Ala-Ala-Phe-COSBn) (SEQ ID NO: 6) was obtained by the same procedures as in Example 7 except that PyBOP was changed to DEPBT (1.5 mg, 5 μmol) or HBTU (1.9 mg, 5 μmol). Its yield was 10% for the use of DEPBT and less than 10% for the use of HBTU.

Comparative Example 2

A benzyl thioester form of a peptide (AcNH-Cys-Cys-Glu-His-COSBn) (SEQ ID NO: 8) was obtained in the same way as in Example 9 except that the reaction temperature was changed to 30° C.

The ratio of racemization was 40%.

INDUSTRIAL APPLICABILITY

According to a process of the present invention, a peptide having a carboxyl group at the C-terminus, with protecting groups in the peptide side chains maintained, can be produced for a non-glycosylated peptide or even for a glycopeptide having an oligosaccharide chain, particularly, an oligosaccharide chain with an unprotected hydroxyl group, without influencing its oligosaccharide chain structure. Furthermore, a peptide thioester compound with little C-terminal racemization of the peptide can be produced.

The obtained peptide thioester compound can be allowed to act on a peptide fragment having Cys as an N-terminal amino acid to thereby achieve polymerization. As a result, large glycoproteins having an oligosaccharide chain with a single structure can also be produced.

What is claimed is:

1. A process for producing a peptide thioester compound, comprising:
   (A) forming a peptide by a solid-phase synthesis method using a resin modified with a linker represented by the formula (1) as a solid phase:

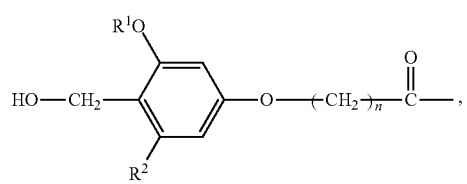

(1)

wherein $R^1$ represents a $C_{1-4}$ alkyl group, $R^2$ represents a hydrogen atom or $C_{1-4}$ alkoxy group, and n represents an integer of 1 to 4;
   (B) cleaving a bond between the solid phase and the peptide with at least one acid selected from dilute hydrochloric acid, dilute sulfuric acid, formic acid, and acetic acid to produce a peptide having a carboxyl group at the C-terminus; and
   (C) reacting a thiol compound with the peptide at −100 to 0° C. in the presence of a condensing agent in a solvent.

2. The production process according to claim 1, wherein the N-terminal amino acid of the peptide is cysteine.

3. The production process according to claim 2, wherein the peptide has a thiol group of the cysteine protected with a fat-soluble protecting group.

4. The production process according to claim 1, wherein the resin modified with a linker represented by the formula (1)

is an amino-PEGA resin having an amino group bonded to the linker represented by the formula (1).

5. The production process according to claim 1, characterized in that the step (B) is performed in the presence of an alcohol.

6. The production process according to claim 5, wherein the alcohol is halogenoalcohol.

7. The production process according to claim 1, wherein the solvent is at least one selected from N,N-dimethylformamide and N-methylpyrrolidone.

8. The production process according to claim 1, wherein the condensing agent is 1-hydroxybenzotriazole/diisopropylcarbodiimide or benzotriazol-1-yloxy-trispyrrolidinophosphonium hexafluorophosphate/diisopropylethylamine.

9. The production process according to claim 1, wherein the peptide is a glycopeptide.

10. A process for producing a peptide having a carboxyl group at the C-terminus, comprising:
  (A) forming a peptide by a solid-phase synthesis method using a resin modified with a linker represented by the formula (1) as a solid phase:

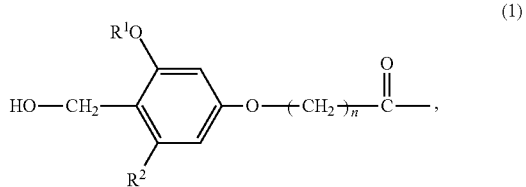

wherein $R^1$ represents a $C_{1-4}$ alkyl group, $R^2$ represents a hydrogen atom or $C_{1-4}$ alkoxy group, and n represents an integer of 1 to 4; and
  (B) cleaving a bond between the solid phase and the peptide with at least one acid selected from dilute hydrochloric acid, dilute sulfuric acid, formic acid, and acetic acid.

11. The production process according to claim 10, wherein the N-terminal amino acid of the peptide is cysteine.

12. The production process according to claim 10, wherein the resin modified with a linker represented by the formula (1) is an amino-PEGA resin having an amino group bonded to the linker represented by the formula (1).

13. The production process according to claim 10, characterized in that the step (B) is performed in the presence of an alcohol.

14. The production process according to claim 13, wherein the alcohol is halogenoalcohol.

15. The production process according to claim 10, wherein the peptide is a glycopeptide.

16. A process for producing a peptide thioester compound, comprising reacting a thiol compound with a peptide having a carboxyl group at the C-terminus in the presence of a condensing agent in a solvent; wherein the N-terminal amino acid of the peptide is cysteine.

17. The production process according to claim 16, wherein the solvent is at least one selected from N,N-dimethylformamide and N-methylpyrrolidone.

18. The production process according to claim 16, wherein the condensing agent is 1-hydroxybenzotriazole/diisopropylcarbodiimide or benzotriazol-1-yloxy-trispyrrolidinophosphonium hexafluorophosphate/diisopropylethylamine.

19. A process for producing a peptide thioester compound, comprising reacting a thiol compound with a peptide having a carboxyl croup at the C-terminus in the presence of a condensing agent in a solvent; wherein the peptide is a glycopeptide.

20. The production process according to claim 19, wherein the solvent is at least one selected from N,N-dimethylformamide and N-methylpyrrolidone.

21. The production process according to claim 19, wherein the condensing agent is 1-hydroxybenzotriazole/diisopropylcarbodiimide or benzotriazol-1-yloxy-trispyrrolidinophosphonium hexafluorophosphate/diisopropylethylamine.

* * * * *

UNITED STATES PATENT AND TRADEMARK OFFICE
CERTIFICATE OF CORRECTION

PATENT NO. : 8,058,394 B2
APPLICATION NO. : 12/295113
DATED : November 15, 2011
INVENTOR(S) : Yasuhiro Kajihara et al.

Page 1 of 1

It is certified that error appears in the above-identified patent and that said Letters Patent is hereby corrected as shown below:

In the Claims

In column 58, claim 19, line 28, before "at the C-terminus in the" replace "croup" with --group--.

Signed and Sealed this
Tenth Day of April, 2012

David J. Kappos
*Director of the United States Patent and Trademark Office*